US012673054B2

(12) United States Patent
Nair et al.

(10) Patent No.: US 12,673,054 B2
(45) **Date of Patent: *Jul. 7, 2026**

(54) SUBSTITUTED NUCLEOSIDE ANALOGS AS PRMT5 INHIBITORS

(71) Applicant: Lupin Limited, Maharastra Mumbai (IN)

(72) Inventors: Prathap Sreedharan Nair, Maharashtra Pune (IN); Ganesh Bhausaheb Gudade, Maharashtra Pune (IN); Shankar Bhaskar Bhagwat, Maharashtra Pune (IN); Amol Maruti Yadav, Maharashtra Pune (IN); Chaitanya Prabhakar Kulkarni, Maharashtra Pune (IN); Milind Dattatraya Sindkhedkar, Maharashtra Pune (IN); Venkata P. Palle, Maharashtra Pune (IN); Rajender Kumar Kamboj, Maharashtra Pune (IN)

(73) Assignee: Lupin Limited, Maharastra Mumbai (IN)

( * ) Notice: Subject to any disclaimer, the term of this patent is extended or adjusted under 35 U.S.C. 154(b) by 663 days.

This patent is subject to a terminal disclaimer.

(21) Appl. No.: 17/782,214

(22) PCT Filed: Dec. 2, 2020

(86) PCT No.: PCT/IB2020/061372

§ 371 (c)(1),
(2) Date: Jun. 3, 2022

(87) PCT Pub. No.: WO2021/111322

PCT Pub. Date: Jun. 10, 2021

(65) Prior Publication Data

US 2023/0066014 A1 Mar. 2, 2023

(30) Foreign Application Priority Data

Dec. 3, 2019 (IN) ............................ 201921049775

(51) Int. Cl.

| | |
|---|---|
| ***A61K 31/473*** | (2006.01) |
| ***A61K 31/437*** | (2006.01) |
| ***A61K 31/4375*** | (2006.01) |
| ***A61K 31/536*** | (2006.01) |
| ***A61P 35/00*** | (2006.01) |

(52) U.S. Cl.

CPC .......... *A61K 31/473* (2013.01); *A61K 31/437* (2013.01); *A61K 31/4375* (2013.01); *A61K 31/536* (2013.01); *A61P 35/00* (2018.01)

(58) Field of Classification Search

CPC ................ A61K 31/473; A61K 31/437; A61K 31/4375; A61K 31/536; A61P 35/00

See application file for complete search history.

(56) References Cited

U.S. PATENT DOCUMENTS

| | | | | |
|---|---|---|---|---|
| 11,459,330 | B2 * | 10/2022 | Nair | C07D 471/04 |
| 11,952,380 | B2 * | 4/2024 | Nair | A61P 35/00 |
| 12,391,695 | B2 * | 8/2025 | Nair | C07D 519/00 |
| 2016/0244475 | A1 | 8/2016 | Tatlock et al. | |
| 2022/0315589 | A1 * | 10/2022 | Nair | A61P 35/00 |

FOREIGN PATENT DOCUMENTS

| | | | |
|---|---|---|---|
| WO | 2011/077133 | A2 | 6/2011 |
| WO | 2011/079236 | A1 | 6/2011 |
| WO | 2014/100695 | A1 | 6/2014 |
| WO | 2014/100716 | A1 | 6/2014 |
| WO | 2014/100719 | A2 | 6/2014 |
| WO | 2014/100730 | A1 | 6/2014 |
| WO | 2014/100734 | A1 | 6/2014 |
| WO | 2014/128465 | A1 | 8/2014 |
| WO | 2014/145214 | A2 | 9/2014 |
| WO | 2015/198229 | A1 | 12/2015 |
| WO | 2015/200677 | A2 | 12/2015 |
| WO | 2015/200680 | A2 | 12/2015 |
| WO | 2016/022605 | A1 | 2/2016 |
| WO | 2016/034671 | A1 | 3/2016 |
| WO | 2016/034673 | A1 | 3/2016 |
| WO | 2016/034675 | A1 | 3/2016 |
| WO | 2016/038550 | A1 | 3/2016 |
| WO | 2016/135582 | A1 | 9/2016 |
| WO | 2016/145150 | A2 | 9/2016 |
| WO | 2016/178870 | A1 | 11/2016 |
| WO | 2017/032840 | A1 | 3/2017 |
| WO | 2018/065365 | A1 | 4/2018 |

(Continued)

OTHER PUBLICATIONS

Sun, Bioorganic and Medicinal Chemistry Letters, vol. 28, Issue 20, Nov. 1, 2018, pp. 3283-3289 (Year: 2018).*
Sun, Bioorganic and Medicinal Chemistry Letters, vol. 28, Issue 20, Nov. 2018, pp. 3283-3289 (Year: 2018).*
PCT International Search Report for PCT Application No. PCT/IB2020/061372 mailed Mar. 25, 2021 (3 pages).
PCT Written Opinion for PCT Application No. PCT/IB2020/061372 mailed Mar. 25, 2021 (5 pages).
Alexander et al., "Abstract 4786: Cellular localization of PRMT5 correlates with poor recurrent free survival in triple-negative breast cancer (TNBC)," AACR; Cancer Research, 2015, 75(15 Suppl).
Emens, "Breast Cancer Immunotherapy: Facts and Hopes," AACR; Clinical Cancer Research, 2018, 24(3):511-520.

(Continued)

*Primary Examiner* — Andrew D Kosar
*Assistant Examiner* — Phillip Matthew Rzeczycki
(74) *Attorney, Agent, or Firm* — Volpe Koenig

(57) ABSTRACT

The invention relates to substituted nucleoside analogues of formula (I), pharmaceutically acceptable salts thereof and pharmaceutical compositions for treating diseases, disorders or conditions associated with the overexpression of PRMT5 enzyme. The invention also relates to methods of treating diseases, disorders or conditions associated with the over-expression of PRMT5 enzyme.

5 Claims, No Drawings

(56) References Cited

FOREIGN PATENT DOCUMENTS

| | | | |
|---|---|---|---|
| WO | 2018/085818 | A1 | 5/2018 |
| WO | 2018/152501 | A1 | 8/2018 |
| WO | 2018/160824 | A1 | 9/2018 |
| WO | 2018/167800 | A1 | 9/2018 |
| WO | 2019/116302 | A1 | 6/2019 |
| WO | 2020/033288 | A1 | 2/2020 |
| WO | 2020/205867 | A1 | 10/2020 |

OTHER PUBLICATIONS

Smil et al., "Discovery of a Dual PRMT5-PRMT7 Inhibitor," ACS Medicinal Chemistry Letters, 2015, 6, 408-412.

Parry et al., "Carbocyclic Analogues of D-Ribose-5-Phosphate: Synthesis and Behavior with 5-Phosphoribosyl α-1-Pyrophosphate Synthetases," Bioorganic & Medicinal Chemistry, 1996, 4(7): 1077-1088.

Saha et al., "Sulforaphane suppresses PRMT5/MEP50 function in epidermal squamos cell carcinoma leading to reduced tumor formation", Carcinogenesis, 2017, 38(8): 827-836.

Stopa et al., "The PRMT5 arginine methyltransferase: many roles in development, cancer and beyond," Cellular and Molecular Life Sciences, 2015, 72, pp. 2041-2059.

Chiang et al., "PRMT5 Is a Critical Regulator of Breast Cancer Stem Cell Function via Histone Methylation and FOXP1 Expression," Cell Reports, 2017, 21: 3498-3513.

Chen et al., "PRMT5 Circular RNA Promotes Metastasis of Urothelial Carcinoma of the Bladder through Sponging miR-30c to Induce Epithelial-Mesenchymal Transition," Clinical Cancer Research, 2018, CCR-18-1270.

Sheng et al., "Methylation of tumor suppressor gene CDH13 and SHP1 promoters and their epigenetic regulation by the UHRF1/PRMT5 complex in endometrial carcinoma," Gynecologic Oncology, 2015, http://dx.doi.org/10.1016/j.ygyno.2015.11.017.

Kanda et al., "Protein arginine methyltransferase 5 is associated with malignant phenotype and peritoneal metastasis in gastric cancer," International Journal of Oncology, 2016, 49:1195-1202.

Jin et al., "Targeting methyltransferase PRMT5 eliminates leukemia stem cells in chronic myelogenous leukemia," The Journal of Clinical Investigation, 2016, 126(10): 3961-3980.

Tamiya et al., "SHARPIN-mediated regulation of protein arginine methyltransferase 5 controls melanoma growth," The Journal of Clinical Investigation, 2018, 128(1): 517-530.

Bao et al., "Overexpression of PRMT5 Promotes Tumor Cell Growth and is Associated with Poor Disease Prognosis in Epithelial Ovarian Cancer," Journal of Histochemistry & Cytochemistry, 2013, 61(3): 206-217.

Wolf et al., "Substituted Sulfaquinoxalines. III. Extension of the Giyoxalate Synthesis of 2-Aminoquinoxaline," Journal of the American Chemical Society, 1949, 71: 6-10.

Cheng et al., "Small Molecule Regulators of Protein Arginine Methyltransferases*," The Journal of Biological Chemistry, 2004, 279(23): 23892-23899.

Chung et al., "Protein Arginine Methyltransferase 5 (PRMT5) Inhibition Induces Lymphoma Cell Death through Reactivation of the Retinoblastoma Tumor Suppressor Pathway and Polycomb Repressor Complex 2 (PRC2) Silencing," The Journal of Biological Chemistry, 2013, 288(49):35534-35547.

Kaushik et al., "Genetic deletion or small molecule inhibition of the arginine methyltransferase PRMT5 exhibit anti-tumoral activity in mouse models of MLL-rearranged AML," Leukemia, Accepted Article Preview 2017, doi: 10.1038/leu.2017.206.

Gulla et al., "Protein Arginine Methyltransferase 5 (PRMT5) has prognostic relevance and is a druggable target in Multiple Myeloma," Leukemia, 2018, 32(4):996-1002.

Wang et al., "Protein Arginine Methyltransferase 5 Suppresses the Transcription of the RB Family of Tumor Suppressors in Leukemia and Lymphoma Cells," Molecular and Cellular Biology, 2008, pp. 6262-6277.

Park et al., "Protein arginine methyltransferase 5 is a key regulator of the MYCN oncoprotein in neuroblastoma cells," Molecular Oncology, 2015, 9:617-627.

Chan-Penebre et al., "A selective inhibitor of PRMT5 with in vivo and in vitro potency in MCL models," Nature Chemical Biology, 2015, 11:432-441.

Yang et al., "Protein arginine methyltransferases and cancer," Nature Reviews Cancer, 2013, 13:37-50.

Banasavadi-Siddegowda et al., "PRMT5-PTEN molecular pathway regulates senescence and self-renewal of primary glioblastoma neurosphere cells," Oncogene, 2017, 36(2):263-274.

Deng et al., "Protein arginine methyltransferase 5 functions as an epigenetic activator of the androgen receptor to promote prostate cancer cell growth," Oncogene, 2017, 36:1223-1231.

Zhang et al., "Arginine methyltransferase inhibitor-1 inhibits sarcoma viability in vitro and in vivo," Oncology Letters, 2018, 16:2161-2166.

Yang et al., "Protein N-arginine methyltransferase 5 promotes the tumor progression and radioresistance of nasopharyngeal carcinoma," Oncology Reports, 2016, 35:1703-1710.

Jeon et al., "Protein arginine methyltransferase 5 is implicated in the aggressiveness of human hepatocellular carcinoma and controls the invasive activity of cancer cells," Oncology Reports, 2018, 40:536-544.

Kumar et al., "Nuclear PRMT5, cyclin D1 and IL-6 are associated with poor outcome in oropharyngeal squamos cell carcinoma patients and is inversely associated with p16-status," Oncotarget, 2017, 8(9):14847-14859.

Zhang et al., "Targeting protein arginine methyltransferase 5 inhibits colorectal cancer growth by decreasing arginine methylation of eIF4E and FGFR3," Oncotarget, 2015, 6(26):22799-22811.

Dong et al., "Arginine methyltransferase inhibitor 1 exhibits antitumor effects against cervical cancer in vitro and in vivo," Pharmazie, 2018, 73:269-273.

Nicholas et al., "PRMT5 Is Unpregulated in Malignant and Metastatic Melanoma and Regulates Expression of MITF and p27 Kip1," PLOS one, 2013, 8(9):e74710.

Kryukov et al., "MTAP deletion confers enhanced dependency on the PRMT5 arginine methyltransferase in cancer cells," Science, 2016, 351(6278): 1214-1217.

Gu et al., "Protein arginine methyltransferase 5 is essential for growth of lung cancer cells," The Biochemical Journal, 2012, 446: 235-241.

Karkhanis et al., "Versatility of PRMT5-induced methylation in growth control and development," Trends in Biochemical Sciences, 2011, 36(12): 633-641.

* cited by examiner

SUBSTITUTED NUCLEOSIDE ANALOGS AS PRMT5 INHIBITORS

CROSS-REFERENCE TO RELATED APPLICATIONS

This application is a National Stage Application of PCT/IB2020/061372, filed 2 Dec. 2020, which claims benefit of Ser. No. 201921049775, filed 3 Dec. 2019 in India and which applications are incorporated herein by reference. To the extent appropriate, a claim of priority is made to the above disclosed applications.

FIELD OF THE INVENTION

The invention relates to substituted nucleoside analogues of formula (I), pharmaceutically acceptable salts thereof and pharmaceutical compositions for treating diseases, disorders or conditions associated with the overexpression of PRMT5 enzyme. The invention also relates to methods of treating diseases, disorders or conditions associated with the overexpression of PRMT5 enzyme.

BACKGROUND TO THE INVENTION

Methylation of proteins is a common post-translational modification that affects the protein's activity and its interaction with other biological molecules. N-methylation typically occurs on the nitrogen atoms of arginine, lysine and histidine residues and there are different families of enzymes that catalyze the methylation reaction, each being specific to the amino acid residue that will be methylated.

A family of 9 enzymes, called Protein Arginine N-Methyl Transferases (PRMTs), are responsible for the methylation of the guanidinium group of arginine. The guanidinium group of arginine bears 2 terminal nitrogen atoms that undergo monomethylation or dimethylation. Depending on the type of dimethylation, the enzymes are further classified as type I or type II. Type I PRMTs catalyse the monomethylation or the asymmetric dimethylation whereas type TT enzymes catalyse the symmetric dimethylation. Some of the substrates that undergo methylation are histones, Sm ribonucleoproteins, MRE11 and p 53 binding protein 1.

The methylation of arginine side-chains has an important role to play in various cell functions that include transcription activation as well as transcription repression, mRNA translation, pre-mRNA splicing, protein trafficking and signal transduction. It also occurs on myriad substrates. The enzymatic activity of the PRMTs hence affects cellular processes like cell proliferation, repair of damaged DNA as well as cell cycle and cell death. It has been shown that PRMT enzyme-mediated hypermethylation leads to certain disease conditions like cancer (Nature Reviews Cancer 2013, 13, p 37; Cellular and Molecular Life Sciences 2015, 72, p 2041; Trends in Biochemical Sciences 2011, 36, p 633).

At present, the most studied type II enzyme is PRMT5, which is conserved across the eukaryotic organisms. Overexpression of PRMT5 is linked with carcinogenesis and decreased patient survival in several human malignancies (Cell Mol Life Sci., 2015, 72, p 2041). PRMT5 directly interacts with proteins often dysregulated or mutated in cancers, hence a putative oncogene (Mol Cell Biol, 2008, 28, p 6262). PRMT5 mediated transcriptional repression of tumor suppressor genes like p 53, RB-1, ST7, or upregulation of Cyclin D1, CDK4, CDK6, eLF4E, MITF, FGFR3 associate with the oncogenesis in both solid tumors and hematological malignancies. PRMT5 is located in the nucleus as well as the cytoplasm and its overexpression has been linked to a wide range of cancers including, but not limited to, glioblastoma multiforme (Oncogene, 2017, 36, p 263), prostate cancer (Oncogene, 2017, 36, p 1223), and pancreatic cancer (Science, 2016, 351, p 1214), mantle cell lymphoma (Nature Chemical Biology, 2015, 11, p 432), non-Hodgkin's lymphomas and diffuse large B-cell lymphoma (Journal of Biological Chemistry, 2013, 288, p 35534), acute myeloid leukemia (Leukemia, 2018, 32, p 499), acute lymphoblastic leukemia (AACR; Cancer Research 2017; 77 (13 Suppl):Abstract nr 1128), multiple myeloma (Leukemia, 2018, 32, p 996), non-small cell lung cancer (The Biochemical Journal, 2012, 446, p 235), small cell lung cancer (AACR; Cancer Research 2017; 77 (13 Suppl):Abstract nr DDT02-04), breast cancer (Cell Reports, 2017, 21, p 3498), triple negative breast cancer (AACR; Cancer Res 2015; 75 (15 Suppl):Abstract nr 4786), gastric cancer (International Journal of Oncology, 2016, 49, p 1195), colorectal cancer (Oncotarget, 2015, 6, p 22799), ovarian cancer (J Histochem Cytochem 2013, 61, p 206), bladder cancer (Clinical Cancer Research, 2018, CCR-18-1270), hepatocellular cancer (Oncology Reports, 2018, 40, p 536), melanoma (PLoS One, 2013, 8, e74710; J Clin Invest. 2018, 128, p 517), sarcoma (Oncology Letters, 2018, 16, p 2161), oropharyngeal squamous cell carcinoma (Oncotarget, 2017, 8, p 14847), chronic myelogenous leukemia (J Clin Invest, 2016, 126, p 3961), epidermal squamous cell carcinoma (Carcinogenesis, 2017, 38, p 827), nasopharyngeal carcinoma (Oncology Reports, 2016, 35, p 1703), neuroblastoma (Molecular Oncology, 2015, 9, p 617), endometrial carcinoma (Gynecol Oncol., 2016, 140, p 145), cervical cancer (Pharmazie, 2018, 73, p 269). These findings have led to further research which show that inhibiting PRMT5 reduces cell proliferation (Molecular and Cellular Biology 2008, 28, p 6262, The Journal of Biological Chemistry 2013, 288, p 35534).

Inhibitors of arginine methyl transferases were first disclosed in 2004 by Cheng et al in the Journal of Biological Chemistry—Vol. 279 (23), p. 23892. Since then, various other compounds and substances having greater selectivity towards either type I or type II arginine methyl transferases have been disclosed. Other publications that disclose small molecules as inhibitors in relation to PRMT5 are: WO2011077133, WO2011079236, WO2014100695, WO2014100716, WO2014100719, WO2014100730, WO2014100734, WO2014128465, WO2014145214, WO2015200677, WO2015200680, WO2015198229, WO2016022605, WO2016034671, WO2016034673, WO2016034675, WO2016038550, WO2016135582, WO2016145150, WO2016178870, WO2017032840, WO2018160824, WO2018152501, WO2018085818, WO2018065365, WO2019116302A1, WO2020033288A1, WO2020205867A1 and ACS Medicinal Chemistry Letters 2015, 6, p 408.

SUMMARY OF THE INVENTION

In accordance with one aspect, the invention provides compound of general formula (I), a stereoisomer thereof, a tautomeric form thereof, or a pharmaceutically acceptable salt thereof, (I)

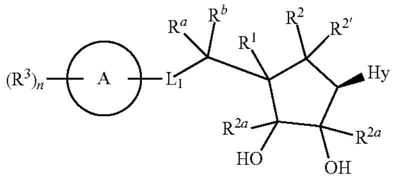

wherein, $L_1$ is selected from —$CR^aR^b$—, —$NR^a$—, S, and O;

$R^a$ and $R^b$ are independently selected at each occurrence from hydrogen, substituted or unsubstituted alkyl, and substituted or unsubstituted cycloalkyl;

ring A is selected from formula (i) to (viii), wherein the substituent $R^3$ on ring A may be substituted on any of the ring C atoms, (i)

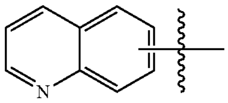

, (ii)

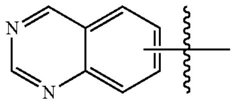

, (iii)

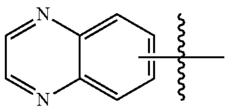

, (iv)

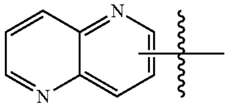

(v)

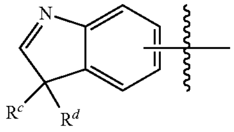

, (vi)

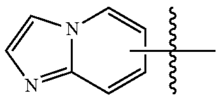

, (vii)

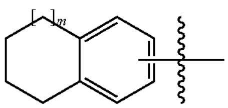

, and (viii)

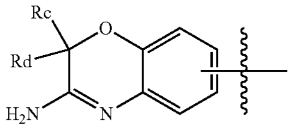

;

$R^c$ and $R^d$ are substituted or unsubstituted alkyl or together with the carbon atoms to which $R^c$ and $R^d$ are attached form a $C_3$-$C_6$ cycloalkyl ring;

Hy is selected from formula (a-1) to (d-1), (a-1)

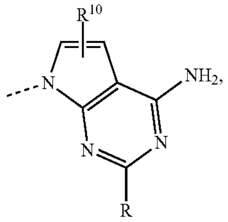

(b-1)

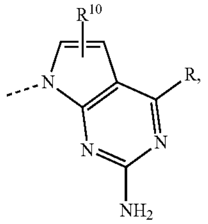

(c-1)

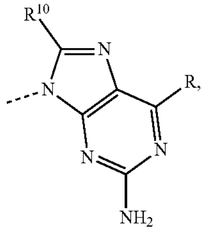

(d-1)

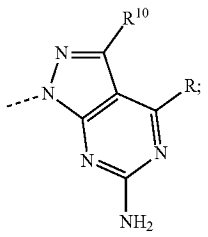

R is selected from —$NR^4R^5$, substituted or unsubstituted alkyl and cycloalkyl;

$R^1$ and $R^2$ together with the carbon atoms to which they are attached form a bond in order to form a —C═C—; or $R^1$ and $R^2$ together with the carbon atoms to which they are attached form a cyclopropane ring;

$R^{2'}$ and $R^{2a}$ which may be same or different and are independently selected at each occurrence from hydrogen and substituted or unsubstituted alkyl;

$R^3$ is independently selected at each occurrence from halogen, cyano, nitro, substituted or unsubstituted alkyl, —$OR^6$, —$NR^7R^8$, substituted or unsubstituted cycloalkyl, —C(O)OH, —C(O)O-alkyl, —C(O)$R^9$, —C(O)$NR^7R^8$, —$NR^7$C(O)$R^9$, substituted or unsubstituted aryl, substituted or unsubstituted heteroaryl, substituted or unsubstituted heterocyclyl and haloalkyl;

$R^4$ and $R^5$ are independently selected from hydrogen, substituted or unsubstituted alkyl, and substituted or unsubstituted cycloalkyl;

$R^6$ is selected from hydrogen, substituted or unsubstituted alkyl, and substituted or unsubstituted cycloalkyl;

$R^7$ and $R^8$ are independently selected from hydrogen, substituted or unsubstituted alkyl, and substituted or unsubstituted cycloalkyl;

$R^9$ is selected from substituted or unsubstituted alkyl and substituted or unsubstituted cycloalkyl;

$R^{10}$ is selected from hydrogen, halogen, and substituted or unsubstituted alkyl;

'm' is an integer ranging from 0 to 1, both inclusive;

'n' is an integer ranging from 0 to 4, both inclusive;

when an alkyl group is substituted, it is substituted with 1 to 4 substituents independently selected from oxo (═O), halogen, cyano, cycloalkyl, aryl, heteroaryl, heterocyclyl, —$OR^{7a}$, —C(═O)OH, —C(═O)O (alkyl), —$NR^{8a}R^{8b}$, —$NR^{8a}C$(═O)$R^{9a}$, and —C(═O)$NR^{8a}R^{8b}$;

when the heteroaryl group is substituted, it is substituted with 1 to 4 substituents independently selected from halogen, cyano, alkyl, haloalkyl, perhaloalkyl, cycloalkyl, heterocyclyl, —$OR^{7a}$, —$NR^{8a}R^{8b}$, —$NR^{7a}C$(═O)$R^{9a}$, —C(═O)$NR^{8a}R^{8b}$;

when the aryl group is substituted, it is substituted with 1 to 4 substituents independently selected from halogen, cyano, alkyl, haloalkyl, perhaloalkyl, cycloalkyl, heterocyclyl, —$OR^{7a}$, —$NR^{8a}R^{8b}$, —$NR^{7a}C$(═O)$R^{9a}$, —C(═O)$NR^{8a}R^{8b}$;

when the cycloalkyl group is substituted, it is substituted with 1 to 4 substituents independently selected from halogen, cyano, alkyl, haloalkyl, perhaloalkyl, —$OR^{7a}$, —$NR^{8a}R^{8b}$, —$NR^{7a}C$(═O)$R^{9a}$, —C(═O)$NR^{8a}R^{8b}$;

$R^{7a}$ is selected from hydrogen, alkyl, perhaloalkyl, and cycloalkyl;

$R^{8a}$ and $R^{8b}$ are each independently selected from hydrogen, alkyl, and cycloalkyl; and $R^{9a}$ is selected from alkyl and cycloalkyl.

The details of one or more embodiments of the invention set forth in below are only illustrative in nature and not intended to limit to the scope of the invention. Other features, objects and advantages of the inventions will be apparent from the description and claims.

According to one embodiment, the invention provides compounds having the structure of formula (II), a stereoisomer thereof, or a pharmaceutically acceptable salt thereof, (II)

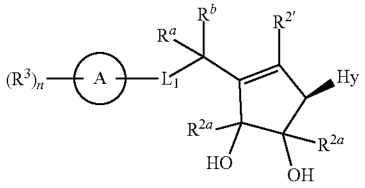

wherein,

Ring A, Hy, $L_1$, $R^{2a}$, $R^{2'}$, $R^a$, $R^b$, $R^3$ and n are as defined herein above.

According to another embodiment, the invention provides compounds having the structure of formula (III), a stereoisomer thereof, or a pharmaceutically acceptable salt thereof, (III)

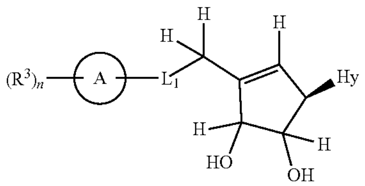

wherein, $L_1$ is —$CR^aR^b$— or O;

Ring A is

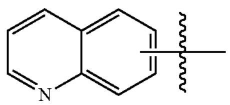

or

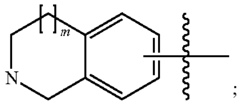

;

Hy is selected from formula (a-1), (b-1) and (d-1), (a-1)

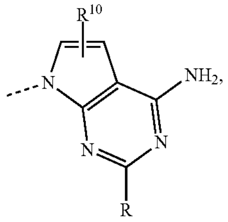

(b-1)

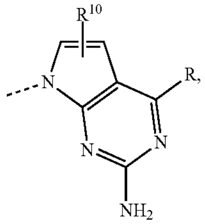

(d-1)

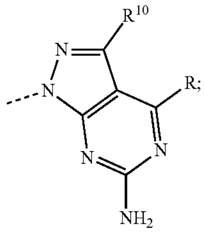

R is selected from —$NR^4R^5$, substituted or unsubstituted alkyl and cycloalkyl; $R^4$ and $R^5$ are independently selected from hydrogen; $R^{2'}$ is hydrogen; $R^3$ is independently selected at each occurrence from halogen, substituted or unsubstituted alkyl, —$OR^6$ and —$NR^7R^8$; $R^7$ and $R^8$ are independently selected from hydrogen; $R^{10}$ is hydrogen; 'm' is 1; 'n' is an integer ranging from 0 to 3, both inclusive;

According to one embodiment, there are provided compounds of formula (I), (II) and (III) wherein the compound is in the form of the free base or is a pharmaceutically acceptable salt thereof.

In any of the above embodiments, R is methyl.

According to another embodiment, there are provided compounds of formula (I), (II) and (III) wherein Hy is selected from,

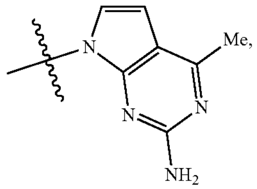

-continued

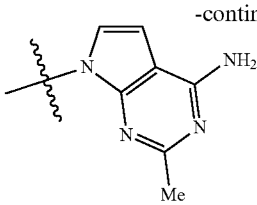

and

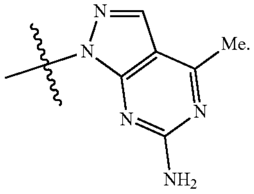

In another aspect of the invention, there are provided compounds of formula (I), (II) and (III) or a pharmaceutically acceptable salt thereof for treating the diseases, disorders, syndromes or conditions associated with PRMT5 enzyme.

In one embodiment of the present invention, there are provided compounds of formula (I), (II) and (III) or a pharmaceutically acceptable salt thereof for treating diseases, disorders, syndromes or conditions by inhibition of PRMT5 enzyme.

In another aspect of the invention, there are provided compounds of formula (I), (II) and (III) or a pharmaceutically acceptable salt thereof for use as a medicament.

In another aspect of the invention, there are provided compounds of (I), (II) and (III) or a pharmaceutically acceptable salt thereof for use in treating the diseases, disorders, syndromes or conditions associated with PRMT5.

In one embodiment of the present invention, there are provided compounds of formula (I), (II) and (III) or a pharmaceutically acceptable salt thereof for use in treating diseases, disorders, syndromes or conditions by the inhibition of PRMT5.

In another aspect of the invention, there is provided a method of inhibiting PRMT5 by using a compound selected from formula (I), (II) and (III) or a pharmaceutically acceptable salt thereof.

In another aspect of the invention, there is provided a method of treating diseases, disorders or conditions associated with PRMT5 by using a compound selected from formula (I), (II) and (III).

In another aspect of the present invention, a method of treating diseases, disorders or conditions is selected from glioblastoma multiforme, prostate cancer, and pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer by using a compound selected from formula (I), (II) and (III) is provided.

In another aspect of the invention, there is provided a use of a compound selected from formula (I), (II) and (III) or a pharmaceutically acceptable salt thereof, for the manufacture of a medicament for treating, the diseases, disorders or conditions associated with PRMT5.

In another aspect, the invention provides a pharmaceutical composition comprising at least one compound of formula (I), (II) and (III) or a pharmaceutically acceptable salt thereof and at least one pharmaceutically acceptable excipient.

In another aspect, the invention provides a pharmaceutical composition comprising a therapeutically effective amount of compound of formula (I), (II) and (III) or a pharmaceutically acceptable salt thereof, for use in treating, the diseases, disorders or conditions associated with PRMT5 by administering to the subject in need thereof.

In another aspect of the present invention, wherein the use of compounds of formula (I), (II) and (III) or a pharmaceutically acceptable salt thereof for the diseases, disorders, syndromes or conditions associated by inhibition of PRMT5 are selected from the group consisting of glioblastoma multiforme, prostate cancer, and pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

In another aspect, the invention provides a pharmaceutical composition comprising a therapeutically effective amount of compound of formula (I), (II) and (III) or a pharmaceutically acceptable salt thereof, for treating the diseases, disorders or conditions associated with PRMT5 by administering to the subject in need thereof.

In another embodiment of the invention the compounds, their stereoisomers or pharmaceutically acceptable salts thereof are:

(1S,2R,5R)-3-(2-(2-Amino-3-chloro-5-fluoroquinolin-7-yl)ethyl)-5-(2-amino-4-methyl-7H-pyrrolo[2,3-d]pyrimidin-7-yl)cyclopent-3-ene-1,2-diol;

(1S,2R,5R)-3-(((2-Amino-3-chloro-5-fluoroquinolin-7-yl)oxy)methyl)-5-(2-amino-4-methyl-7H-pyrrolo[2,3-d]pyrimidin-7-yl)cyclopent-3-ene-1,2-diol;

(1S,2R,5R)-5-(4-Amino-2-methyl-7H-pyrrolo[2,3-d]pyrimidin-7-yl)-3-(((2-amino-3-chloro-5-fluoroquinolin-7-yl)oxy)methyl)cyclopent-3-ene-1,2-diol;

(1S,2R,5R)-3-(2-(2-Amino-3-chloro-5-fluoroquinolin-7-yl)ethyl)-5-(6-amino-4-methyl-1H-pyrazolo[3,4-d]pyrimidin-1-yl)cyclopent-3-ene-1,2-diol;

(1S,2R,5R)-5-(4-Amino-2-methyl-7H-pyrrolo[2,3-d]pyrimidin-7-yl)-3-(((6-(difluoromethyl)-1,2,3,4-tetrahydroisoquinolin-8-yl)oxy)methyl)cyclopent-3-ene-1,2-diol;

(1S,2R,5R)-5-(4-Amino-2-methyl-7H-pyrrolo[2,3-d]pyrimidin-7-yl)-3-(2-(6-(difluoromethyl)-1,2,3,4-tetrahydroisoquinolin-8-yl)ethyl)cyclopent-3-ene-1,2-diol;

(1S,2R,5R)-5-(4-Amino-2-methyl-7H-pyrrolo[2,3-d]pyrimidin-7-yl)-3-(2-(2-amino-3-chloro-5-fluoroquinolin-7-yl)ethyl)cyclopent-3-ene-1,2-diol, and (1S,2R,5R)-5-(2-Amino-4-methyl-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol.

DETAILED DESCRIPTION OF THE INVENTION

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, for example ($C_1$-$C_6$)alkyl or ($C_1$-$C_4$)alkyl, representative groups include e.g., methyl, ethyl, n-propyl, 1-methylethyl (isopropyl), n-butyl, n-pentyl and the like. Unless set forth or recited to the contrary, all alkyl groups described or claimed herein may be straight chain or branched.

The term "haloalkyl" refers to an alkyl group as defined above that is substituted by one or more halogen atoms as defined above. For example ($C_1$-$C_6$)haloalkyl or ($C_1$-$C_4$) haloalkyl. Suitably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Suitably, a polyhaloalkyl is substituted with up to 12 halogen atoms. Non-limiting Examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched.

The term "alkoxy" denotes an alkyl group attached via an oxygen linkage to the rest of the molecule. Representative examples of such groups are $—OCH_3$ and $—OC_2H_5$. Unless set forth or recited to the contrary, all alkoxy groups described or claimed herein may be straight chain or branched.

The term "alkoxyalkyl" refers to an alkoxy group as defined above directly bonded to an alkyl group as defined above, e.g., $—CH_2—O—CH_3$, $—CH_2—O—CH_2CH_3$, $—CH_2CH_2—O—CH_3$ and the like.

The term "cycloalkyl" refers to a non-aromatic mono or multicyclic ring system having 3 to 12 carbon atoms, such as ($C_3$-$C_{10}$)cycloalkyl, ($C_3$-$C_6$)cycloalkyl, cyclopropyl, cyclobutyl, cyclopentyl, cyclohexyl and the like. Examples of multicyclic cycloalkyl groups include, but are not limited to, perhydronaphthyl, adamantyl and norbornyl groups, bridged cyclic groups or spirobicyclic groups, e.g., spiro(4,4)non-2-yl and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(S), and one or two carbon atoms(S) in the heterocyclic ring or heterocyclyl may be interrupted with $—CF_2—$, —C(O)—, —S(O)—, $S(O)_2$ etc. In addition, heterocyclic ring may also be fused with aromatic ring. Non-limiting Examples of heterocyclic rings include azetidinyl, benzopyranyl, chromanyl, decahydroisoquinolyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinylsulfoxide, thiamorpholinylsulfoneindoline, benzodioxole, tetrahydroquinoline, tetrahydrobenzopyran and the like. The heterocyclic ring may be attached by any atom of the heterocyclic ring that results in the creation of a stable structure.

The term "heteroaryl" unless otherwise specified, refers to a substituted or unsubstituted 5- to 14-membered aromatic heterocyclic ring with one or more heteroatom(S) independently selected from N, O or S. The heteroaryl may be a mono-, bi- or tricyclic ring system. The heteroaryl ring may be attached by any atom of the heteroaryl ring that results in the creation of a stable structure. Non-limiting Examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like.

The compounds of the present invention may have one or more chiral centers. The absolute stereochemistry at each chiral center may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are non-superimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of formula (I).

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; c) lessening the disease, disorder or condition or at least one of its clinical or subclinical symptoms or (d) relieving the disease, i.e., causing regression of the state, disorder or condition or at least one of its clinical or subclinical symptoms.

The term "inhibitor" refers to a molecule that binds to an enzyme to inhibit the activity of the said enzyme either partially or completely.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a disease, disorder or condition, is sufficient to cause the effect in the subject, which is the purpose of the administration. The "therapeutically effective amount" will vary depending on the compound, the disease and its severity and the age, weight, physical condition, and responsiveness of the subject to be treated.

Pharmaceutically Acceptable Salts

The compounds of the invention may form salts with acid or base. The compounds of invention may be sufficiently basic or acidic to form stable nontoxic acid or base salts, administration of the compound as a pharmaceutically acceptable salt may be appropriate. Non-limiting Examples of pharmaceutically acceptable salts are inorganic, organic acid addition salts formed by addition of acids including hydrochloride salts. Non-limiting Examples of pharmaceutically acceptable salts are inorganic, organic base addition salts formed by addition of bases. The compounds of the invention may also form salts with amino acids. Pharmaceutically acceptable salts may be obtained using standard procedures well known in the art, for example by reacting sufficiently basic compound such as an amine with a suitable acid.

Screening of the compounds of invention for PRMT5 inhibitory activity can be achieved by using various in vitro and in vivo protocols mentioned herein below or methods known in the art.

Pharmaceutical Compositions

The invention relates to pharmaceutical compositions containing the compounds of the formula (I), or pharmaceutically acceptable salts thereof disclosed herein. In particular, pharmaceutical compositions containing a therapeutically effective amount of at least one compound of formula (I) described herein and at least one pharmaceutically acceptable excipient (such as a carrier or diluent). Preferably, the contemplated pharmaceutical compositions include the compound(s) described herein in an amount sufficient to inhibit PRMT5 to treat the diseases described herein when administered to a subject.

The subjects contemplated include, for example, a living cell and a mammal, including human. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes pharmaceutical agent that does not itself induce the production of antibodies harmful to the individual receiving the composition, and which may be administered without undue toxicity.

Examples of suitable carriers or excipients include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerytritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for Example, in a sachet.

The pharmaceutical compositions may be in conventional forms, for example, capsules, tablets, caplets, orally disintegrating tablets, aerosols, solutions, suspensions, or products for topical application.

The route of administration may be any route which effectively transports the active compound of the invention to the appropriate or desired site of action. Suitable routes of administration include, but are not limited to, oral, oral inhalation, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, caplet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 1000 mg by oral administration and 1 μg to 5000 μg by inhalation according to the potency of the active component or mode of administration.

Those skilled in the relevant art can determine suitable doses of the compounds for use in treating the diseases and disorders described herein. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the PRMT5 inhibitor can range from about 0.1 to about 30.0 mg/kg by oral administration. Mode of administration, dosage forms, suitable pharmaceutical excipients, diluents or carriers can also be well used and adjusted by those skilled in the art. All changes and modifications envisioned are within the scope of the invention.

The invention provides compound of formula (I) and pharmaceutical compositions thereof as protein arginine methyl transferase-5 (PRMT5) inhibitors for treating the diseases, disorders or conditions associated with overexpression of PRMT5. The invention further provides a method of treating diseases, disorders or conditions associated with overexpression of PRMT5 in a subject in need thereof by administering to the subject a therapeutically effective amount of a compound or a pharmaceutical composition of the invention.

In another aspect, the invention relates to a method of treating diseases, disorders or conditions associated with the overexpression of PRMT5. In this method, a subject in need of such treatment is administered a therapeutically effective amount of a compound of formula (I) or a pharmaceutically acceptable salt thereof as described herein.

In one embodiment of the present invention, the diseases, disorders, or conditions associated with the overexpression of PRMT5 are cancer.

In another embodiment, the invention provides a method of treating cancers, particularly, glioblastoma multiforme, prostate cancer, pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

It is to be understood that the invention encompasses the compounds of formula (I) or pharmaceutically acceptable salts thereof for use in the treatment of a disease or disorder mentioned herein.

It is to be understood that the invention encompasses the compounds of formula (I) or pharmaceutically acceptable salts thereof in the manufacture of a medicament for treating a disease or disorder mentioned herein.

A compound, its tautomeric form, its stereoisomer, its pharmaceutically acceptable salt, its polymorph, its solvate, its combination with suitable medicament, its pharmaceutical composition thereof as described hereinabove wherein the compound of general formula (I), is selected from the group consisting of:

(1S,2R,5R)-3-(2-(2-Amino-3-chloro-5-fluoroquinolin-7-yl)ethyl)-5-(2-amino-4-methyl-7H-pyrrolo[2,3-d]pyrimidin-7-yl)cyclopent-3-ene-1,2-diol;

(1S,2R,5R)-3-(((2-Amino-3-chloro-5-fluoroquinolin-7-yl)oxy)methyl)-5-(2-amino-4-methyl-7H-pyrrolo[2,3-d]pyrimidin-7-yl)cyclopent-3-ene-1,2-diol;

(1S,2R,5R)-5-(4-Amino-2-methyl-7H-pyrrolo[2,3-d]pyrimidin-7-yl)-3-(((2-amino-3-chloro-5-fluoroquinolin-7-yl)oxy)methyl)cyclopent-3-ene-1,2-diol;

(1S,2R,5R)-3-(2-(2-Amino-3-chloro-5-fluoroquinolin-7-yl)ethyl)-5-(6-amino-4-methyl-1H-pyrazolo[3,4-d]pyrimidin-1-yl)cyclopent-3-ene-1,2-diol;

(1S,2R,5R)-5-(4-Amino-2-methyl-7H-pyrrolo[2,3-d]pyrimidin-7-yl)-3-(((6-(difluoromethyl)-1,2,3,4-tetrahydroisoquinolin-8-yl)oxy)methyl)cyclopent-3-ene-1,2-diol;

(1S,2R,5R)-5-(4-Amino-2-methyl-7H-pyrrolo[2,3-d]pyrimidin-7-yl)-3-(2-(6-(difluoromethyl)-1,2,3,4-tetrahydroisoquinolin-8-yl)ethyl)cyclopent-3-ene-1,2-diol;

(1S,2R,5R)-5-(4-Amino-2-methyl-7H-pyrrolo[2,3-d]pyrimidin-7-yl)-3-(2-(2-amino-3-chloro-5-fluoroquinolin-7-yl)ethyl)cyclopent-3-ene-1,2-diol and (1S,2R,5R)-5-(2-Amino-4-methyl-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol or pharmaceutically acceptable salt thereof.

The compound of formula described herein may be prepared by techniques known in the art. In addition, the compound of formula described herein may be prepared by following the reaction sequence as depicted in Schemes provided below. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art, are also within the scope of the present invention. All the isomers of the compound of formula in described in these schemes, unless otherwise specified, are also encompassed within the scope of this invention.

Scheme-1 illustrates the synthesis of compound of formula 11. Compound of formula 1 (where PG=Protecting group such as but not limited to TBDPS, TBDMS etc.), is prepared by following the procedure described in Purinergic Signaling (2015) 11:371-387. Mitsunobu reaction of compound of formula 1 with compound of formula 2 (X=—Cl, —Br) using various azo dicarboxylate reagents such as but not limited to DEAD or DIAD in presence of phosphine such as but not limited to $PPh_3$ gives the compound of formula 3. Typically, these reactions are run in ethereal solvents such as THF, MeTHF, dioxane, or similar solvents at temperatures ranging from 0° C. to 25° C. Compound of formula 4 is formed upon treatment of compound of formula 3 with fluoride ions such as but not limited to TBAF. Typically these reactions are done in ethereal solvents such as THF, MeTHF, dioxane, or similar solvents at temperatures ranging from 0° C. to 40° C. Oxidation of compound of formula 4 with various oxidizing agents such as but not limited to Dess-Martin periodinane can furnish the compound of formula 5. Typically these reactions can be run in halogenated solvents such as $CH_2Cl_2$, $CHCl_3$, dichloroethane or similar solvents at temperatures ranging from 0° C. to 40° C. Reagents such as but not limited to methyltriphenylphosphonium bromide in presence of a base such as but not limited to KO$^t$Bu, NaO$^t$Bu, LiHMDS, NaHMDS, or KHMDS when treated with compound of formula 5 affords compound of formula 6. Typically these reactions are done in ethereal solvents such as THF, MeTHF, dioxane, or similar solvents at temperatures ranging from 0° C. to 25° C. Compound of formula 8 can be synthesized by hydroboration of compound of formula 6 with suitable boranes such as but not limited to 9-BBN followed by addition of inorganic base such as but not limited to tripotassium phosphate or $Cs_2CO_3$, in presence of Pd catalyst such as but not limited to Pd(dppf)$Cl_2$ or Pd-118 and compound of formula 7 (Y=—Br, —I), which was synthesized by following the procedure reported in Journal of the American Chemical Society, 1949, vol. 71, p. 6.7. Typically these reactions are done in ethereal solvents such as THF, MeTHF, dioxane, or similar solvents at temperatures ranging from 25° C. to 70° C.

Scheme-1

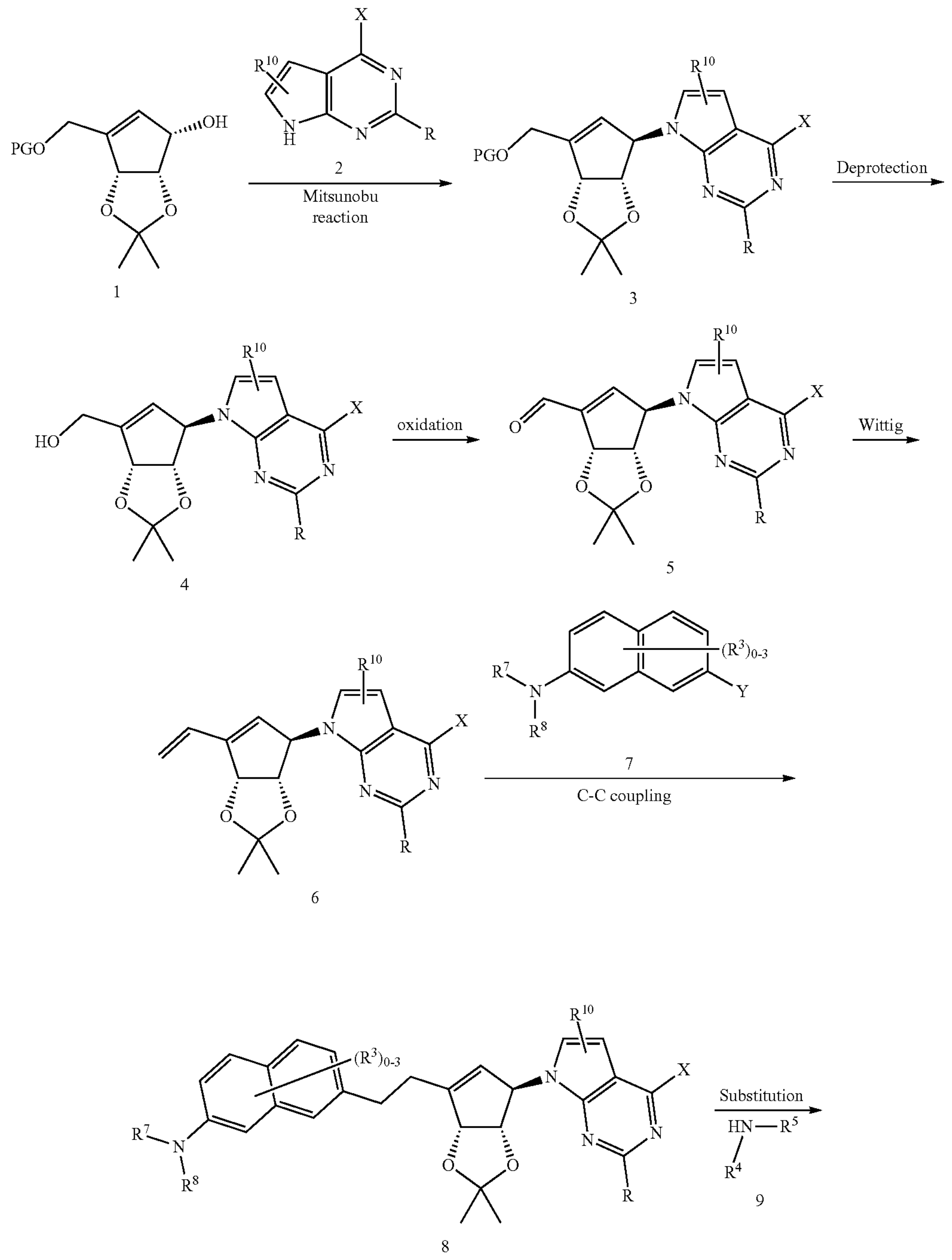

-continued

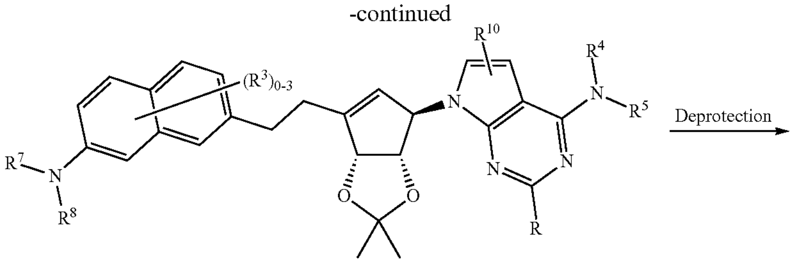

10

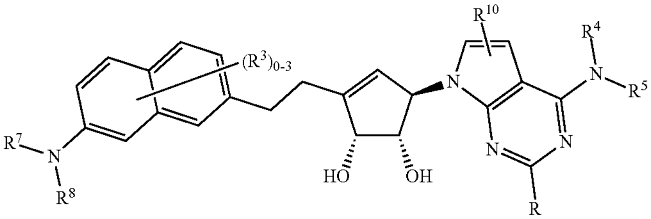

11

Compound of formula 9 (where $R^4$ and $R^5$ is defined herein above) upon treatment with compound of formula 8 affords compound of formula 10. Acetonide deprotection of compound of formula 10 with acids such as but not limited to HCl or TFA affords compound of formula 11. Typically, these reactions are run at temperatures ranging from 25° C. to 50° C. Compounds at every step may be purified by standard techniques such as column chromatography, crystallization, reverse phase HPLC, or SFC.

Scheme-2 illustrates the synthesis of compound of formula 16. Iodination of compound of formula 4 with various reagents such as but not limited to Iodine/$PPh_3$/Imidazole can furnish the compound of formula 12. Typically these reactions can be run in halogenated solvents such as but not limited to $CH_2Cl_2$ at temperatures ranging from 0° C. to 25° C. for about 30 mins to 3 h. Base such as but not limited to $Cs_2CO_3$ when treated with compound of formula 12 in presence of compound of formula 13 (synthesis is described herein below in scheme-7; $PG_1$=-Boc) affords compound of formula 14. Typically, these reactions are done in solvents such as DMF DMAc, or similar solvents at temperatures ranging from 0° C. to 25° C. for about 30 mins to 3 h.

Scheme-2

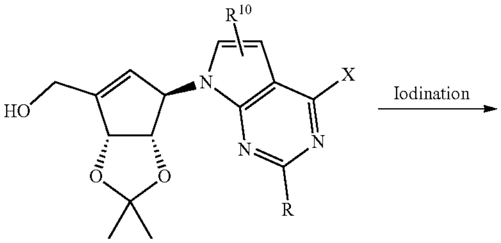

4

-continued

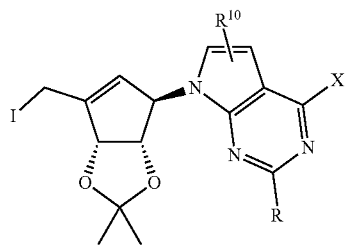

12

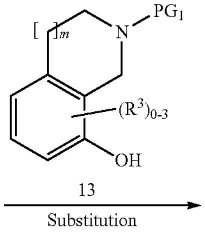

13

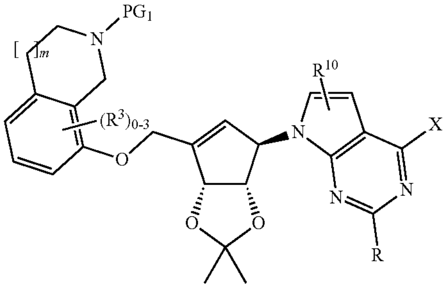

14

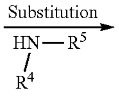

9

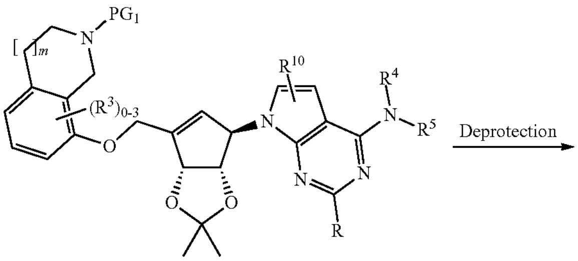

15

-continued

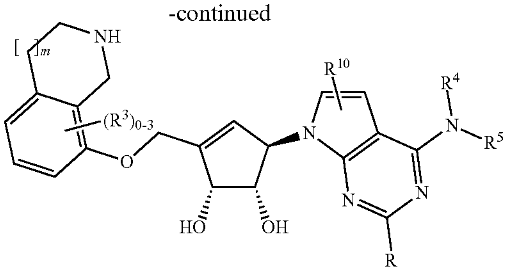

16

Compound of formula 9 (where $R^4$ and $R^5$ is defined herein above) upon treatment with compound of formula 14 affords compound of formula 15. Typically, these reactions are done in ethereal solvents such as dioxane, or similar solvents at temperatures ranging from 100° C. to 140° C. for about 8-16 h. Deprotection of compound of formula 15 with acids such as but not limited to HCl or TFA affords compound of formula 16. Typically these reactions are run at temperatures ranging from 25° C. to 50° C. for about 1-5 h. Compounds at every step may be purified by standard techniques such as column chromatography, crystallization, reverse phase HPLC, or SFC.

Scheme-3 illustrates the synthesis of compound of formula 20. Compound of formula 18 can be synthesized by hydroboration of compound of formula 6 with suitable boranes such as but not limited to 9-BBN followed by addition of inorganic base such as but not limited to tripotassium phosphate in presence of Pd catalyst such as but not limited to $Pd(dppf)Cl_2$ or Pd-118 and compound of formula 17 (synthesis is described herein below in scheme-7; Y=—Br, —I; $PG_1$=-Boc). Typically, these reactions are done in ethereal solvents such as THF, MeTHF, dioxane, or similar solvents at temperatures ranging from 25° C. to 70° C. for about 1-8 h.

Scheme-3

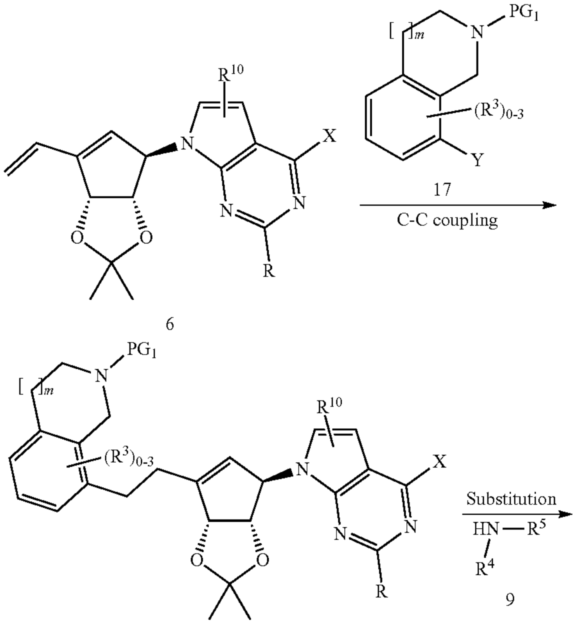

6

17

18

9

-continued

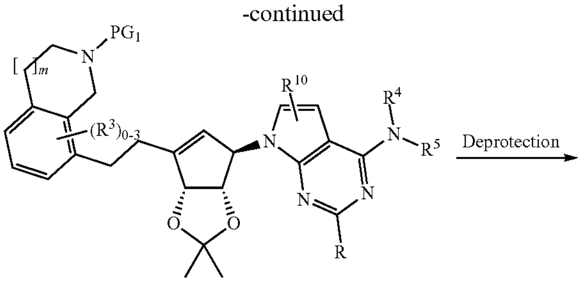

19

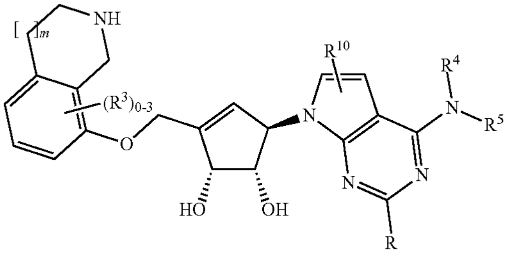

20

Compound of formula 9 (where $R^4$ and $R^5$ is defined herein above) upon treatment with compound of formula 18 affords compound of formula 19. Typically, these reactions are done in ethereal solvents such as dioxane or similar solvents at temperatures ranging from 100° C. to 140° C. for about 8-16 h. Deprotection of compound of formula 19 with acids such as but not limited to HCl or TFA affords compound of formula 20. Typically these reactions are run at temperatures ranging from 25° C. to 50° C. for about 1-5 h. Compounds at every step may be purified by standard techniques such as column chromatography, crystallization, reverse phase HPLC, or SFC.

Scheme-4 illustrates the synthesis of compound of formula 28. Oxidation of compound of formula 21 (which was synthesized as described in Bio-organic and medicinal Chemistry, 1996, 4(7), 1077-1088) with various oxidizing agents such as but not limited to Dess-Martin periodinane can furnish the compound of formula 22. Typically, these reactions can be run in halogenated solvents such as $CH_2Cl_2$, $CHCl_3$, dichloroethane or similar solvents at temperatures ranging from 0° C. to 25° C. for about 1-3 h. Reagents such as but not limited to methyltriphenylphosphonium bromide in presence of a base such as but not limited to n-BuLi when treated with compound of formula 22 provides compound of formula 23. Typically these reactions are done in ethereal solvents such as THF, MeTHF, dioxane, or similar solvents at temperatures ranging from 0° C. to 10° C. for about 10 min to 2 h. Compound of formula 24 can be synthesized by hydroboration of compound of formula 23 with suitable boranes such as but not limited to 9-BBN followed by addition of inorganic base such as but not limited to tripotassium phosphate, in presence of Pd catalyst such as but not limited to $Pd(dppf)Cl_2$ or Pd-118 and compound of formula 7 (Y=—Br, —I), which was synthesized by following the procedure reported in Journal of the American Chemical Society, 1949, vol. 71, p. 6.7. Typically these reactions are done in ethereal solvents such as THF, MeTHF, dioxane, or similar solvents at temperatures ranging from 0° C. to 25° C. for about 1 h to 4 h.

Scheme-4
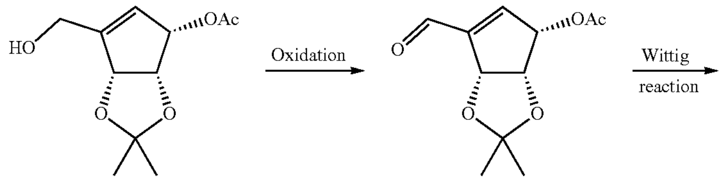
21 22
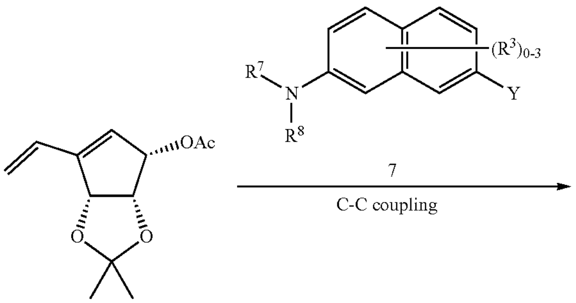
23
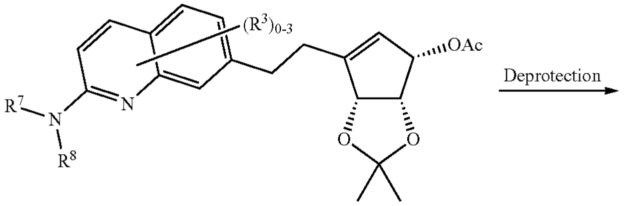
24
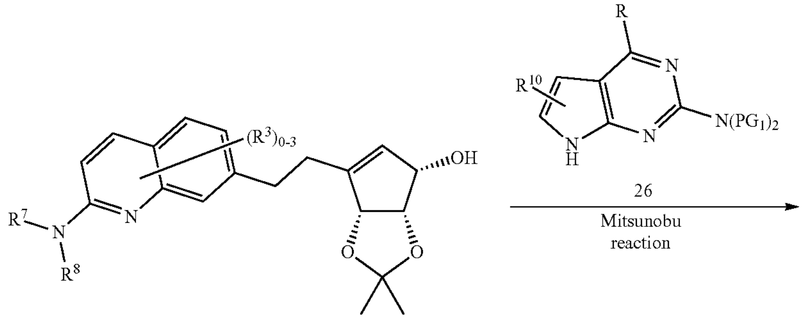
25
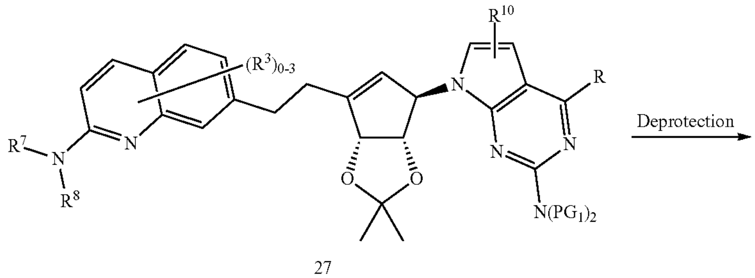
27

-continued

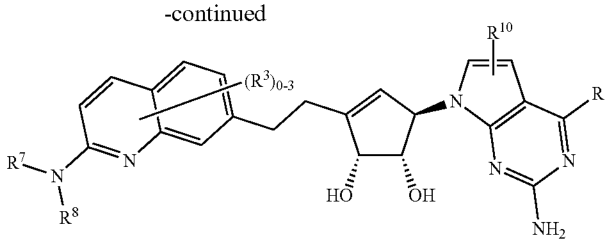

28

Deprotection of compound of formula 24 with bases such as but not limited to $K_2CO_3$ or $Na_2CO_3$ affords compound of formula 25. Typically these reactions are run in protic solvents such as but not limited to MeOH or EtOH at temperatures ranging from 0° C. to 25° C. for about 1 h to 3 h. Mitsunobu reaction of compound of formula 25 with compound of formula 26 ($PG_1$=–Boc) using various azodicarboxylate reagents such as but not limited to DEAD or DIAD in presence of phosphine such as but not limited to $PPh_3$ gives the compound of formula 27. Typically, these reactions are run in ethereal solvents such as THF, MeTHF, dioxane, or similar solvents at temperatures ranging from 0° C. to 25° C. for about 8 h to 48 h. Deprotection of compound of formula 27 with acids such as but not limited to HCl or TFA affords compound of formula 28. Typically these reactions are run at temperatures ranging from 25° C. to 60° C. for about 1 h to 6 h. Compounds at every step may be purified by standard techniques such as column chromatography, crystallization, reverse phase HPLC, or SFC.

Scheme-5 illustrates the synthesis of compound of formula 33.

Scheme-5

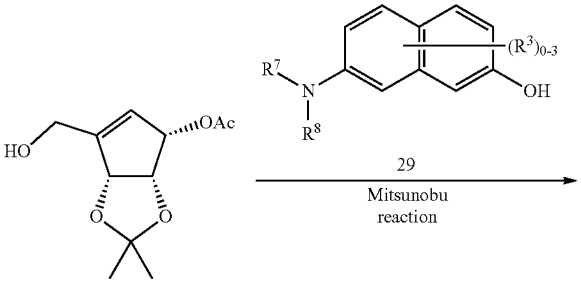

21

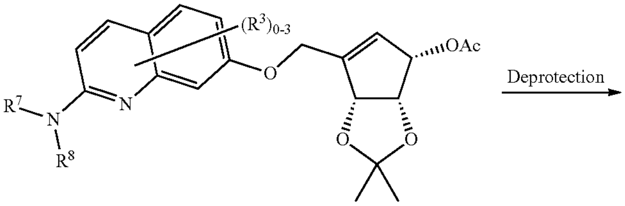

30

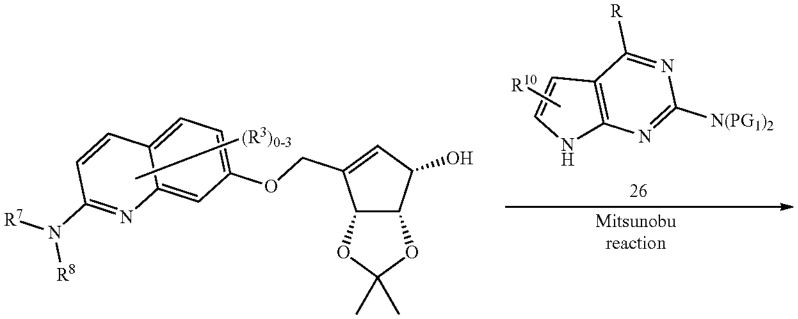

31

-continued

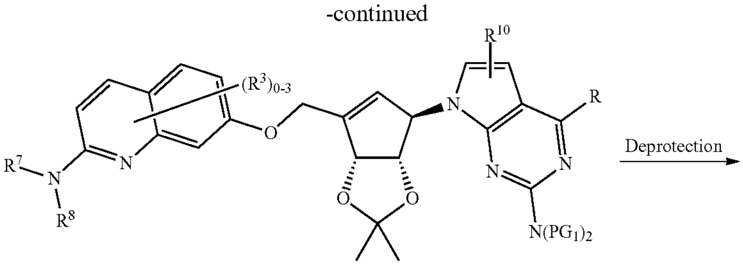

32

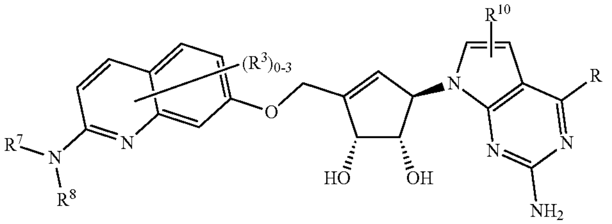

33

Mitsunobu reaction of compound of formula 21 with compound of formula 29 using various azodicarboxylate reagents such as but not limited to DEAD or DIAD in presence of phosphine such as but not limited to $PPh_3$ gives the compound of formula 30. Typically, these reactions are run in ethereal solvents such as THF, MeTHF, dioxane, or similar solvents at temperatures ranging from 0° C. to 25° C. for about 8 h to 16 h. Deprotection of compound of formula 30 with bases such as but not limited to $K_2CO_3$ or $Na_2CO_3$ affords compound of formula 31. Typically these reactions are run in protic solvents such as but not limited to MeOH or EtOH at temperatures ranging from 0° C. to 25° C. for about 1 h to 3 h. Mitsunobu reaction of compound of formula 31 with compound of formula 26 ($PG_1$=-Boc) using various azo dicarboxylate reagents such as but not limited to DEAD or DIAD in presence of phosphine such as but not limited to $PPh_3$ gives the compound of formula 32. Typically, these reactions are run in ethereal solvents such as THF, MeTHF, dioxane, or similar solvents at temperatures ranging from 0° C. to 25° C. for about 8 h to 16 h. Deprotection of compound of formula 32 with acids such as but not limited to HCl or TFA affords compound of formula 33. Typically these reactions are run at temperatures ranging from 25° C. to 60° C. for about 1 h to 6 h. Compounds at every step may be purified by standard techniques such as column chromatography, crystallization, reverse phase HPLC, or SFC.

Scheme-6 illustrates the synthesis of compound of formula 36.

Scheme-6

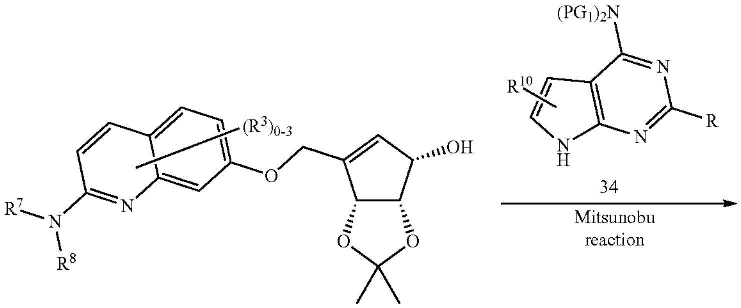

31

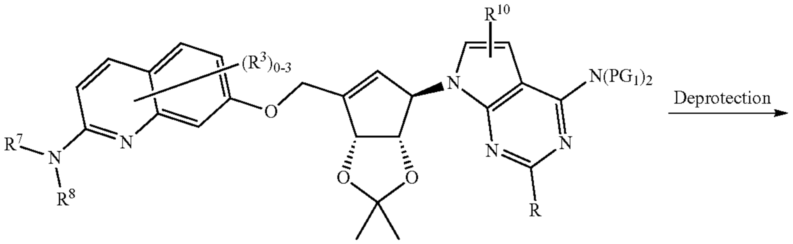

35

-continued

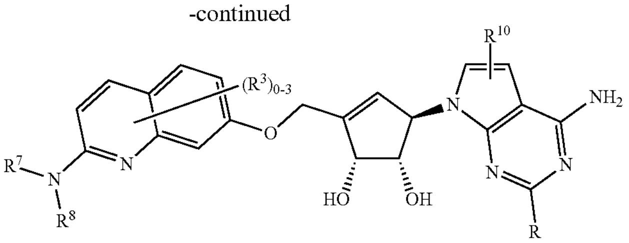

36

Mitsunobu reaction of compound of formula 31 with compound of formula 34 ($PG_1$=–Boc) using various azo dicarboxylate reagents such as but not limited to DEAD or DIAD in presence of phosphine such as but not limited to $PPh_3$ gives the compound of formula 35. Typically, these reactions are run in ethereal solvents such as THF, MeTHF, dioxane, or similar solvents at temperatures ranging from 0° C. to 25° C. for about 8 h to 16 h. Deprotection of compound of formula 35 with acids such as but not limited to HCl or TFA affords compound of formula 36. Typically these reactions are run at temperatures ranging from 25° C. to 60° C. for about 1 h to 6 h. Compounds at every step may be purified by standard techniques such as column chromatography, crystallization, reverse phase HPLC, or SFC.

Scheme-7 illustrates the synthesis of compound of formula 48. Treating compound of formula 37 with compound of formula 37a affords compound of formula 38. Typically, these reactions are run in solvent such as but not limited to toluene at temperatures ranging from 100° C. to 120° C. for about 1 h to 5 h.

Scheme-7

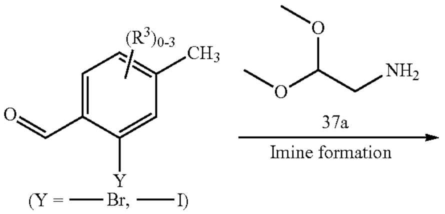

37a

37

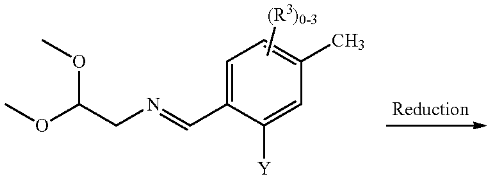

38

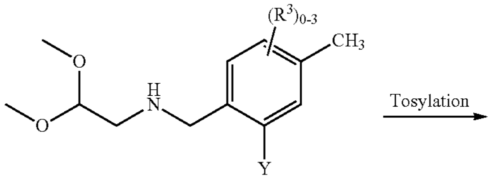

39

-continued

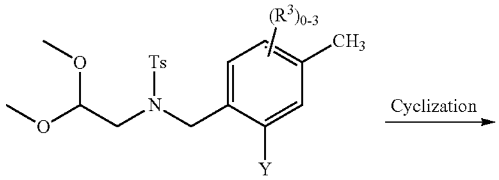

40

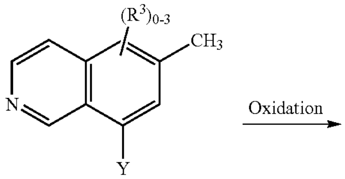

41

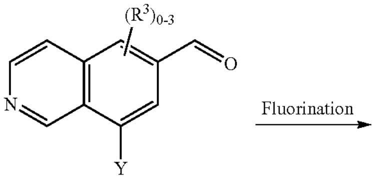

42

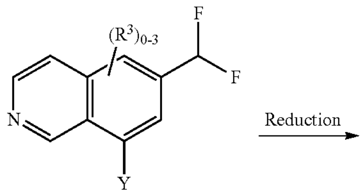

43

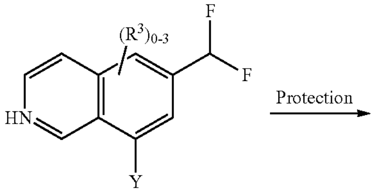

44

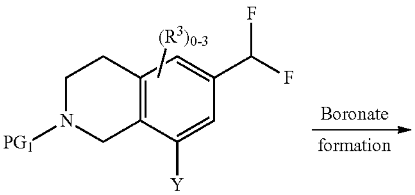

45

-continued

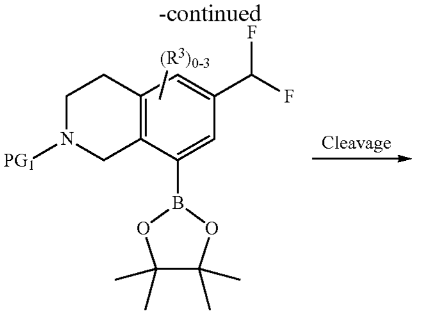

46

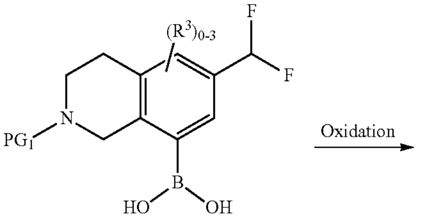

47

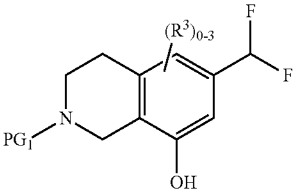

48

Reduction of compound of formula 38 with reducing agent such as but not limited to $NaBH_4$ gives compound of formula 39. Typically these reactions are run in protic solvents such as but not limited to MeOH or EtOH at temperatures ranging from 0° C. to 25° C. for about 1 h to 3 h. Tosylation of compound of formula 39 with reagents such as but not limited to TsCl/Pyridine provides compound of formula 40. Typically, these reactions are run in halogenated solvents such as but not limited to $CH_2Cl_2$ at temperatures ranging from 0° C. to 25° C. for about 5 h to 16 h. Cyclization of compound of formula 40 with reagents such as but not limited to $AlCl_3$ affords compound of formula 41. Typically these reactions are run in halogenated solvents such as but not limited to $CH_2Cl_2$ at temperatures ranging from 0° C. to 25° C. for about 5 h to 16 h. Oxidation of compound of formula 41 with oxidizing agents such as but not limited to selenium dioxide gives compound of formula 42. Typically these reactions are run in hydrocarbon solvents such as but not limited to 1,2-dichlorobenzene at temperatures ranging from 150° C. to 180° C. for about 2 h to 8 h. Fluorination of compound of formula 42 with fluorinating agents such as but not limited to DAST gives compound of formula 43. Typically, these reactions are run in halogenated solvents such as but not limited to $CH_2Cl_2$ at temperatures ranging from 0° C. to 25° C. for about 5 h to 16 h. Reduction of compound of formula 43 with reducing agent such as but not limited to $NaBH_4$ gives compound of formula 44. Typically, these reactions are run in solvents such as but not limited to acetic acid at temperatures ranging from 0° C. to 25° C. for about 1 h to 3 h. Protection of compound of formula 44 with reagents such as but not limited to Boc-anhydride/$NEt_3$ gives compound of formula 45. Typically, these reactions are run in halogenated solvents such as but not limited to $CH_2Cl_2$ at temperatures ranging from 0° C. to 25° C. for about 1 h to 3 h. Compound of formula 46 can be synthesized by treating compound of formula 45 with suitable boron reagents such as but not limited to bispinacoloto diboron followed by addition of inorganic base such as but not limited to potassium acetate, in presence of Pd catalyst such as but not limited to Pd(dppf)$Cl_2$. Typically these reactions are done in ethereal solvents such as dioxane, or similar solvents at temperatures ranging from 100° C. to 110° C. for about 1 h to 4 h. Compound of formula 47 can be synthesized by treating compound of formula 46 with suitable reagents such as but not limited to sodium per iodate followed by addition of inorganic acid such as but not limited to HCl. Typically these reactions are done in solvents such as acetone, or similar solvents at temperatures ranging from 0° C. to 25° C. for about 1 h to 4 h. Oxidation of compound of formula 47 with oxidizing agents such as but not limited to hydrogen peroxide in presence of acid such as but not limited to citric acid gives compound of formula 48. Typically, these reactions are run at temperatures ranging from 0° C. to 25° C. for about 1 h to 3 h.

Scheme-8

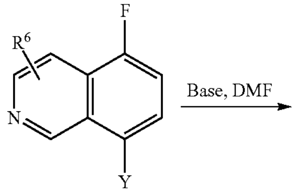

49

Y = Br, I

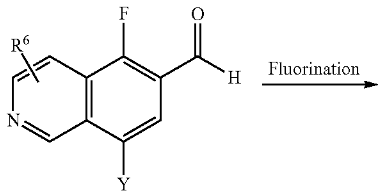

50

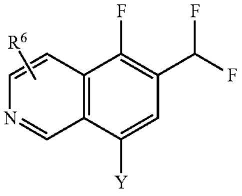

51

Scheme-8 illustrates the synthesis of compound of formula 51. Formylation reaction of compound of formula 49 with formylating agent such as but not limited to DMF in presence of hindered base such as but not limited to LDA gives the compound of formula 50. Typically these reactions are run in ethereal solvents such as THF, MeTHF, dioxane, or similar solvents at temperatures ranging from −78° C. to 0° C. Compound of formula 50 upon treatment with nucleophilic fluorinating agents such as but not limited to DAST can give compound of formula 51. Typically, these reactions can be run in halogenated solvents such as $CH_2Cl_2$, $CHCl_3$ or similar solvents at temperatures ranging from 0° C. to 25° C.

Scheme-9

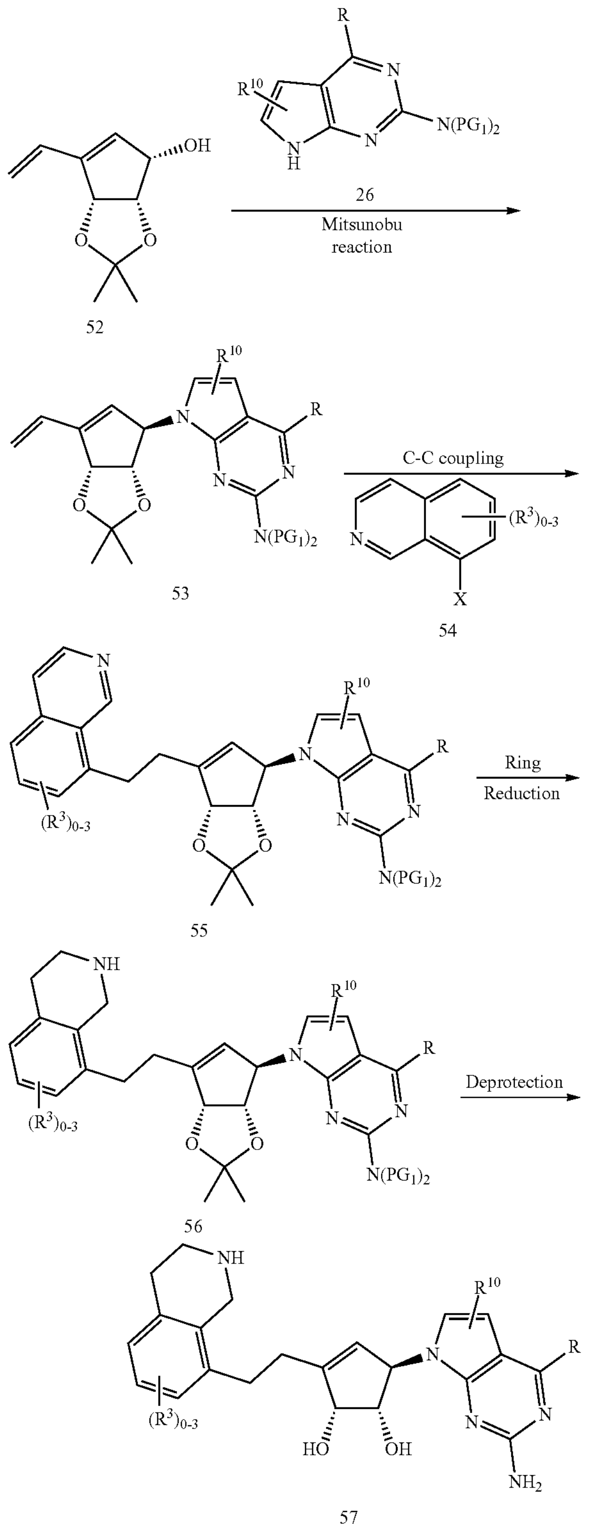

26, 52, 53, 54, 55, 56, 57

Scheme-9 illustrates the synthesis of compound of formula 57. Mitsunobu reaction of compound of formula 52 with compound of formula 26 ($PG_1$=-Boc) using various azodicarboxylate reagents such as but not limited to DEAD or DIAD in presence of phosphine such as but not limited to $PPh_3$ gives the compound of formula 53. Typically these reactions are run in ethereal solvents such as for example THF, MeTHF, dioxane, or similar solvents at temperatures ranging from 0° C. to 25° C. Compound of formula 55 can be synthesized by hydroboration of compound of formula 53 with suitable boranes such as but not limited to 9-BBN followed by addition of inorganic base such as but not limited to tripotassium phosphate or $Cs_2CO_3$, in presence of Pd catalyst such as but not limited to Pd(dppf)$Cl_2$ or Pd-118 and compound of formula 54 (Y═Br, —I). Typically these reactions are done in ethereal solvents such as THF, MeTHF, dioxane, or similar solvents and run at temperatures ranging from 25° C. to 70° C. Compound of formula 55 upon treatment with reducing agents such as but not limited to $NaBH_4$ affords compound of formula 56. Typically these reactions are done in acidic solvents such as for example acetic acid at temperatures ranging from 0° C. to 25° C. Additionally, deprotection of compound of formula 56 with acids such as but not limited to HCl or TFA affords compound of formula 57. Typically these reactions are run at temperatures ranging from 25° C. to 50° C. Compounds at every step may be purified by standard techniques such as column chromatography, crystallization, reverse phase HPLC or SFC.

ABBREVIATIONS

The following abbreviations may be used herein:

AcOH=Acetic acid
Aq.=aqueous
9-BBN=9-Borabicyclononane
Boc=tert-Butoxycarbonyl
t-Bu or tBu=tert-Butyl
$Cs_2CO_3$=Cesium Carbonate
$CHCl_3$=Chloroform
DAST=Diethylaminosulphur trifluoride
$CH_2Cl_2$ or DCM=Dichloromethane
DMP=Dess Martin Periodinane
DEAD=Diethyl azodicarboxylate
DIAD=Diisopropyl azodicarboxylate
DMAP=4-Dimethylaminopyridine
DMF=N,N-Dimethylformamide
DMSO=Dimethylsulphoxide
DMSO-$d_6$=Deuterated dimethylsulphoxide
Et=ethyl
EtOH=Ethanol
EtOAc=Ethyl acetate
g=gram
$K_2CO_3$=Potassium carbonate
KOH=Potassium hydroxide
KO$^{t}$Bu=Potassium tert-butoxide
KHMDS=Potassium bis(trimethylsilyl)amide
LCMS=Liquid chromatography mass spectrometry
mg=milligram
Me=Methyl
MeOH=Methanol
MeOD=Deuterated methanol
MsCl=Methanesulphonyl chloride
$MgSO_4$=Magnesium sulphate
NaH=Sodium hydride
NaO$^{t}$Bu=Sodium tert-butoxide
$NaHCO_3$=Sodium bicarbonate
$Na_2SO_4$=Sodium sulphate
$Na_2S_2O_3$=Sodium thiosulphate
$Na_2SO_3$=Sodium sulphite
NaHMDS=Sodium bis(trimethylsilyl)amide
NMR=Nuclear magnetic resonance Ph=phenyl
Pd-118=[1,1'-Bis(di-tert-butylphosphino)ferrocene]dichloropalladium(II)
$PdCl_2$(dppf)=[1,1'-Bis(diphenylphosphino)ferrocene]dichloropalladium(II)
PCC=Pyridinium chlorochromate
PMB=p-Methoxybenzyl
PTSA=p-Toluenesulphonic acid
Rt=Retention time
rt=room temperature
Sat.=saturated
SFC=Supercritical fluid chromatography
TLC=Thin layer chromatography
TBAF=Tetrabutylammonium fluoride
TsCl=p-Toluenesulphonyl chloride
TBDMS=tert-Butyldimethylsilyl
TBDPS=tert-Butyldiphenylsilyl
$Et_3N$ or $NEt_3$ or TEA=Trimethylamines
TFA=Trifluoroacetic acid
THF=Tetrahydrofuran
Ts=p-Toluenesulphonyl

INTERMEDIATES

7-Bromo-3-chloro-5-fluoroquinolin-2-amine

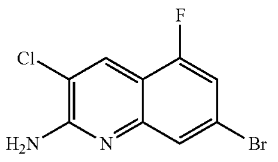 [SMILES: Nc1nc2cc(Br)cc(F)c2cc1Cl]

The title compound was prepared by following an analogous reaction protocol as described in WO2019/116302 A1.

7-Bromo-3-chloro-5-fluoro-N,N-bis(4-methoxybenzyl)quinolin-2-amine

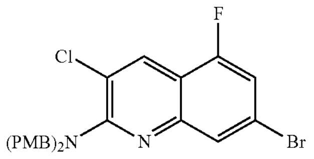

To a stirred suspension of 7-bromo-3-chloro-5-fluoroquinolin-2-amine (7.0 g, 25.4 mmol) in DMF (90 mL) was added sodium hydride (2.54 g, 63.5 mmol) at 0° C. The resulting mixture was stirred at 0° C. for 15 min. 1-(Chloromethyl)-4-methoxybenzene (8.27 mL, 61.0 mmol) was added dropwise under $N_2$ atmosphere. The reaction mixture was then stirred for 5 h at 25° C. The resulting mixture was poured onto ice water (100 mL). The solid precipitated out was filtered, washed with water (200 ml) and dried under vacuum. It was further co-evaporated with toluene and dried in vacuo to afford 7-bromo-3-chloro-5-fluoro-N,N-bis(4-methoxybenzyl)quinolin-2-amine (13 g, 99%) as an off white solid. $^1$H NMR (400 MHz, DMSO-d6) δ 8.39 (d, J=0.9 Hz, 1H), 7.76 (t, J=1.3 Hz, 1H), 7.52 (dd, J=9.4, 1.7 Hz, 1H), 7.29-7.23 (m, 4H), 6.91-6.84 (m, 4H), 4.60 (s, 4H), 3.71 (s, 6H); LCMS m/z=514.68, 516.68 (M+, M+2; 100%).

3-Chloro-5-fluoro-N,N-bis(4-methoxybenzyl)-7-(4,4,5,5-tetramethyl-1,3,2-dioxaborolan-2-yl)quinolin-2-amine

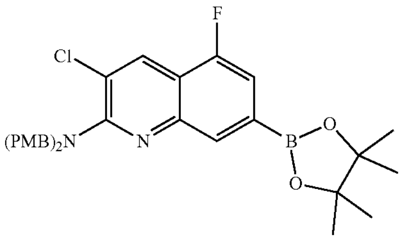

A mixture of 7-bromo-3-chloro-5-fluoro-N,N-bis(4-methoxybenzyl)quinolin-2-amine (2.200 g, 4.27 mmol), $PdCl_2$(dppf) (0.312 g, 0.427 mmol), bis(pinacolato)diboron (1.3 g, 5.12 mmol), potassium acetate (0.712 g, 7.25 mmol) and DMSO (5 ml) was heated at 80° C. for 30 min. in preheated oil bath. The resulting mixture was slowly poured onto ice cold water (50 ml) and extracted with ethyl acetate (50 ml). Layers were separated, and the organic layer was washed with brine (50 ml) and dried over anhydrous $Na_2SO_4$. The organic layer was filtered and concentrated in vacuo to give 2.5 g of crude compound. This residue was purified by combiflash ($R_f$200, Teledyne/Isco) instrument onto a Redisep® $R_f$-column with gradient elution (0 to 10%) of ethyl acetate in petroleum ether to afford 3-chloro-5-fluoro-N,N-bis(4-methoxybenzyl)-7-(4,4,5,5-tetramethyl-1,3,2-dioxaborolan-2-yl)quinolin-2-amine (2 g, 83%) as an off white solid. $^1$H NMR (400 MHz, DMSO-d6) δ 8.44 (d, J=0.9 Hz, 1H), 7.81 (t, J=0.9 Hz, 1H), 7.31-7.28 (m, 1H), 7.27-7.23 (m, 4H), 6.89-6.84 (m, 4H), 4.59 (d, J=12.3 Hz, 4H), 3.70 (s, 6H), 1.17 (s, 12H).

2-(Bis(4-methoxybenzyl)amino)-3-chloro-5-fluoroquinolin-7-ol

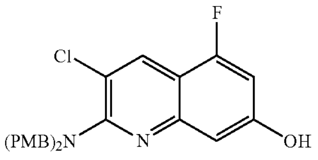

To a stirred solution of 3-chloro-5-fluoro-N,N-bis(4-methoxybenzyl)-7-(4,4,5,5-tetramethyl-1,3,2-dioxaborolan-2-yl)quinolin-2-amine (1.6 g, 2.84 mmol) in THF (35 ml), was added glacial acetic acid (0.325 ml, 5.69 mmol) dropwise at 0° C. The mixture was stirred at 0° C. for 1 h. An aq. solution of hydrogen peroxide (1.742 ml, 17.06 mmol) was added slowly and stirred the reaction mixture for 16 h at 25° C. The reaction mixture was diluted with ethyl acetate (50 ml) and added water (50 ml). Layers were separated and the organic layer was washed with aq. sat. $Na_2SO_3$ (50 ml) and brine (50 ml) successively. The organic layer was dried over anhydrous sodium sulphate, filtered, and concentrated in vacuo to give 1.8 g of crude compound. This crude residue was purified by combiflash ($R_f$200, Teledyne/Isco) instrument onto a Redisep® $R_f$-column with gradient elution (0 to 25%) of ethyl acetate in petroleum ether to afford the title compound (1 g, 78%) as an off white solid.

$^1$H NMR (400 MHz, DMSO-d6) δ 10.46 (d, J=0.8 Hz, 1H), 8.21 (d, J=0.7 Hz, 1H), 7.29-7.22 (m, 4H), 6.90-6.83 (m, 4H), 6.82-6.75 (m, 2H), 4.51 (s, 4H), 3.71 (s, 6H); LCMS m/z=452.92 (M+; 50%).

tert-Butyl 4-(bis(tert-butoxycarbonyl)amino)-2-methyl-7H-pyrrolo[2,3-d]pyrimidine-7-carboxylate

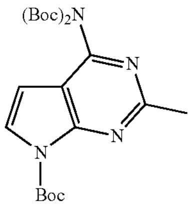

To a solution of commercially available 2-methyl-7H-pyrrolo[2,3-d]pyrimidin-4-amine (0.400 g, 2.70 mmol) in acetonitrile (10 ml) and methylene chloride (10 ml), was added di-tert-butyl dicarbonate (6.27 ml, 27.0 mmol) and DMAP (0.066 g, 0.540 mmol) at 25° C. The resulting mixture was stirred at 25° C. for 16 h. Volatiles were removed in vacuo and the crude residue was purified by combiflash ($R_f$200, Teledyne/Isco) instrument onto a Redisep® $R_f$ column with gradient elution (0 to 20%) of ethyl acetate in petroleum ether to afford the title compound (0.7 g, 57.8%) as an off-white solid. $^1$H NMR (400 MHz, Chloroform-d) δ 7.61 (d, J=4.1 Hz, 1H), 6.44 (d, J=4.1 Hz, 1H), 2.86 (s, 3H), 1.70 (s, 9H), 1.43 (s, 18H); LCMS m/z=448.42 (M+; 50%).

tert-Butyl (tert-butoxycarbonyl)(2-methyl-7H-pyrrolo[2,3-d]pyrimidin-4-yl)carbamate H

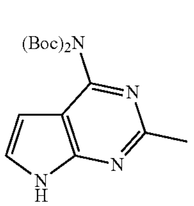

To a solution of tert-butyl 4-(bis(tert-butoxycarbonyl)amino)-2-methyl-7H-pyrrolo[2,3-d]pyrimidine-7-carboxylate (0.7 g, 1.561 mmol) in MeOH (7 ml) was added triethylamine (2.393 ml, 17.17 mmol) at 25° C. The resulting mixture was stirred at 60° C. for 18 h. Volatiles were removed in vacuo and the crude residue was purified by combiflash ($R_f$200, Teledyne/Isco) instrument onto a Redisep® $R_f$ column with gradient elution (0 to 15%) of ethyl acetate in petroleum ether to afford the title compound (0.4 g, 73.6%) as an off-white solid. $^1$H NMR (400 MHz, DMSO-d6) δ 12.05 (s, 1H), 7.49 (dd, J=3.6, 2.2 Hz, 1H), 6.27 (dd, J=3.6, 1.7 Hz, 1H), 2.59 (s, 3H), 1.41 (s, 18H); LCMS m/z=349.41 (M+1; 10%).

(E)-1-(2-Bromo-4-methylphenyl)-N-(2,2-dimethoxyethyl)methanimine

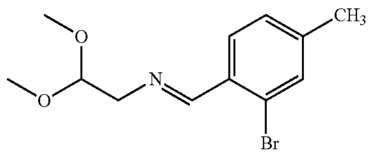

A mixture of 2-bromo-4-methylbenzaldehyde (73 g, 367 mmol) and 2,2-dimethoxyethan-1-amine (47.9 ml, 440 mmol) in toluene (450 ml) was heated to 120° C. with a Dean-Stark apparatus for 4 h. Volatiles were removed in vacuo and this crude compound was carried forward for the next step without further purification. $^1$H NMR (400 MHz, DMSO-d6) δ 8.54 (s, 1H), 7.83 (d, J=8.0 Hz, 1H), 7.54 (dd, J=1.7, 0.9 Hz, 1H), 7.29-7.25 (m, 1H), 4.64 (t, J=5.4 Hz, 1H), 3.74 (dd, J=5.4, 1.4 Hz, 2H), 3.30 (s, 6H), 2.34 (s, 3H).

N-(2-Bromo-4-methylbenzyl)-2,2-dimethoxyethan-1-amine

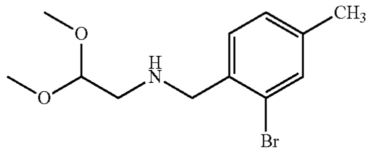

To a solution of (E)-1-(2-bromo-4-methylphenyl)-N-(2,2-dimethoxyethyl)methanimine (105 g, 367 mmol) in ethanol (820 ml), was added sodium borohydride (20.82 g, 550 mmol) portion-wise at 0° C. The resulting mixture was stirred at 25° C. for 2 h. Acetone (100 ml) was slowly added to quench the reaction. Volatiles were removed in vacuo and the crude residue was purified by combiflash ($R_f$200, Teledyne/Isco) instrument onto a Redisep® $R_f$ column with gradient elution (0 to 2%) of methanol in dichloromethane to afford the title compound (83 g, 78%) as an off-white solid. $^1$H NMR (400 MHz, DMSO-d6) δ 7.44-7.40 (m, 1H), 7.36 (d, J=7.7 Hz, 1H), 7.20-7.15 (m, 1H), 4.41 (t, J=5.5 Hz, 1H), 3.72 (s, 2H), 3.25 (s, 6H), 2.58 (d, J=5.5 Hz, 2H), 2.28 (s, 3H); LCMS m/z=288.1 (M+; 100%).

N-(2-Bromo-4-methylbenzyl)-N-(2,2-dimethoxyethyl)-4-methylbenzenesulfonamide

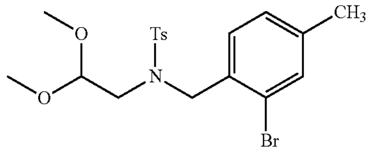

To a stirred solution of N-(2-bromo-4-methylbenzyl)-2,2-dimethoxyethan-1-amine (83 g, 288 mmol) in DCM (1000 ml), was added pyridine (116 ml, 1440 mmol) followed by solution of p-toluenesulfonyl chloride (93 g, 490 mmol) in DCM (300 ml) dropwise at 25° C. The resulting mixture was stirred for 16 h. The reaction mixture was diluted with water (1000 ml) and extracted with methylene chloride (1000 ml). Layers were separated and the organic layer was washed with brine (500 ml). The organic layer was dried over anhydrous sodium sulphate, filtered, and concentrated in vacuo to give 130 g of crude compound. This crude residue was purified by combiflash ($R_f$200, Teledyne/Isco) instrument onto a Redisep® $R_f$ column with gradient elution (0 to 25%) of ethyl acetate in petroleum ether to afford the title compound (120 g, 94%) as a colourless oil. $^1$H NMR (400 MHz, Chloroform-d) δ 7.81-7.71 (m, 2H), 7.42-7.27 (m, 4H), 7.16-7.06 (m, 1H), 4.52 (s, 2H), 4.37 (t, J=5.3 Hz, 1H), 3.31 (d, J=5.4 Hz, 2H), 3.23 (s, 6H), 2.45 (s, 3H), 2.32 (s, 3H); LCMS m/z=507.05; 10%).

8-Bromo-6-methylisoquinoline

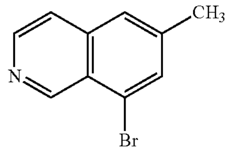

To an ice cooled solution of aluminum chloride (217 g, 1628 mmol) in DCM (1400 ml) was added a solution of N-(2-bromo-4-methylbenzyl)-N-(2,2-dimethoxyethyl)-4-methylbenzenesulfonamide (120 g, 271 mmol) in DCM (600 ml) dropwise at 0° C. The resulting mixture was allowed to warm to 25° C. and stirred at this temperature for 16 h. The reaction mixture was diluted with cold water (2 lit.) and 500 ml of DCM and stirred for 1 h. Layers were separated, and the aqueous layer was again extracted with DCM (500 ml×2). The combined organic layer was washed with brine (500 ml), dried over anhydrous sodium sulphate, filtered, and concentrated in vacuo to give 80 g of crude compound. This crude residue was purified by combiflash ($R_f$200, Teledyne/Isco) instrument onto a Redisep® $R_f$ column with gradient elution (0 to 50%) of ethyl acetate in petroleum ether to afford the title compound (50 g, 83%) as an off white solid. $^1$H NMR (400 MHz, Chloroform-d) δ 9.54 (s, 1H), 8.57 (d, J=5.7 Hz, 1H), 7.71 (d, J=1.5 Hz, 1H), 7.61-7.51 (m, 2H), 2.54 (s, 3H); LCMS m/z=222, 224 (M+, M+2; 100%).

8-Bromoisoquinoline-6-carbaldehyde

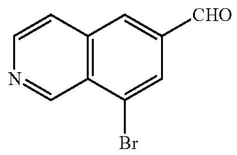 [SMILES: O=Cc1cc(Br)c2cnccc2c1]

A suspension of selenium dioxide (28.0 g, 252 mmol) and 8-bromo-6-methylisoquinoline (20 g, 90 mmol) in 1,2-dichlorobenzene (120 ml) was heated at 180° C. for 7 h. The reaction mixture was diluted with 25% MeOH in DCM (500 ml) and filtered through a celite bed, washed with 25% MeOH in DCM (500 ml). The filtrate was concentrated under reduced pressure and the residue was purified by combiflash ($R_f$200, Teledyne/Isco) instrument onto a Redisep® $R_f$ column with gradient elution (0 to 70%) of ethyl acetate in petroleum ether to afford the title compound (5.1 g, 23.99%) as an off white solid. $^1$H NMR (400 MHz, DMSO-d6) δ 10.17 (s, 1H), 9.57 (d, J=1.0 Hz, 1H), 8.80 (d, J=5.6 Hz, 1H), 8.68 (t, J=1.1 Hz, 1H), 8.29 (d, J=1.4 Hz, 1H), 8.15 (dd, J=5.6, 0.9 Hz, 1H); GCMS m/z=235.07, 237.07 (M+, M+2; 100%).

8-Bromo-6-(difluoromethyl)isoquinoline

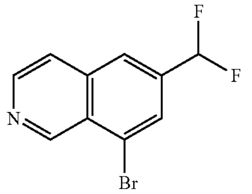 [SMILES: FC(F)c1cc(Br)c2cnccc2c1]

To a stirred solution of 8-bromoisoquinoline-6-carbaldehyde (5 g, 21.18 mmol) in DCM (120 ml) was slowly added DAST (28.0 ml, 212 mmol) at 0° C. The resulting mixture was stirred at 0° C. for 15 mins & then at 25° C. for 16 h. The reaction was diluted with DCM (50 ml) and quenched with cold aqueous saturated $NaHCO_3$ solution (100 ml). The reaction mixture was stirred at 25° C. until $CO_2$ evolution ceased (~20 mins.). Layers were separated and the aqueous layer was again extracted with DCM (50 ml×2). The combined organic layer was washed with brine (50 ml), dried over anhydrous sodium sulphate, filtered, and concentrated in vacuo to give 5.1 g of a crude compound. This crude residue was purified by combiflash ($R_f$200, Teledyne/Isco) instrument onto a Redisep® $R_f$ column with gradient elution (0 to 30%) of ethyl acetate in petroleum ether to afford the title compound (3.3 g, 60.4%) as an off white solid. $^1$H NMR (400 MHz, Chloroform-d) δ 9.70 (s, 1H), 8.73 (d, J=5.7 Hz, 1H), 8.04-7.96 (m, 2H), 7.75 (d, J=5.8 Hz, 1H), 6.81 (t, J=55.8 Hz, 1H); GCMS m/z=257.04, 259.04 (M+, M+2; 100%).

8-Bromo-6-(difluoromethyl)-1,2,3,4-tetrahydroisoquinoline

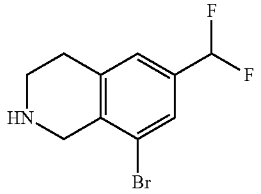 [SMILES: FC(F)c1cc(Br)c2c(c1)CCNC2]

To a stirred solution of 8-bromo-6-(difluoromethyl)isoquinoline (2.22 g, 8.60 mmol) in acetic Acid (50 ml) was added $NaBH_4$ (1.139 g, 30.1 mmol) in portions at 25° C. The reaction was stirred at 25° C. for 1.5 h. Volatiles were removed in vacuo at 40° C. and the crude residue was diluted with DCM (50 ml) and washed with sat. aq. $NaHCO_3$ (100 ml). Layers were separated and the organic layer was washed with brine (50 ml). The organic layer was dried over anhydrous sodium sulphate, filtered, and concentrated in vacuo to give 2.2 g of crude compound, which was carried to next step without further purification. $^1$H NMR (400 MHz, Chloroform-d) δ 7.54 (s, 1H), 7.22 (s, 1H), 6.58 (t, J=56.3 Hz, 1H), 4.02 (s, 2H), 3.13 (t, J=5.9 Hz, 2H), 2.86 (t, J=5.9 Hz, 2H).

tert-Butyl 8-bromo-6-(difluoromethyl)-3,4-dihydroisoquinoline-2(1H)-carboxylate

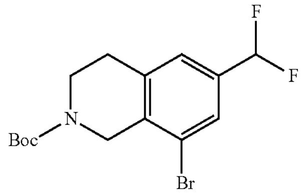 [SMILES: CC(C)(C)OC(=O)N1CCc2cc(C(F)F)cc(Br)c2C1]

To a stirred solution of 8-bromo-6-(difluoromethyl)-1,2,3,4-tetrahydroisoquinoline (5 g, 19.08 mmol) in DCM (45 ml) was added $Et_3N$ (5.32 ml, 38.2 mmol) and di-tert-butyl dicarbonate (5.32 ml, 22.89 mmol) at 0° C. The resulting mixture was stirred at 25° C. for 2 h. The reaction mixture was diluted with water (100 ml) and extracted with DCM (100 ml×2). Layers were separated and the organic layer was washed with brine (100 ml). The organic layer was dried over anhydrous sodium sulphate, filtered, and concentrated in vacuo to give 6.2 g of a crude compound. This crude residue was purified by combiflash ($R_f$200, Teledyne/Isco) instrument onto a Redisep® $R_f$ column with gradient elution (0 to 7%) of ethyl acetate in petroleum ether to afford the title compound (5.8 g, 84%) as an off white solid. $^1$H NMR (400 MHz, Chloroform-d) δ 7.59 (s, 1H), 7.26 (s, 1H), 6.59 (t, J=56.3 Hz, 1H), 4.58 (s, 2H), 3.67 (t, J=5.8 Hz, 2H), 2.90 (t, J=5.9 Hz, 2H), 1.53 (s, 9H).

tert-Butyl 6-(difluoromethyl)-8-(4,4,5,5-tetramethyl-1,3,2-dioxaborolan-2-yl)-3,4-dihydroisoquinoline-2(1H)-carboxylate

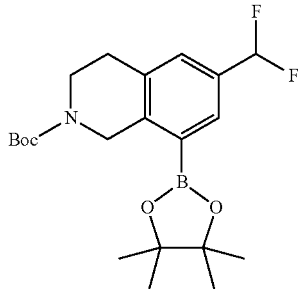 [SMILES: CC(C)(C)OC(=O)N1CCc2cc(C(F)F)cc(B3OC(C)(C)C(C)(C)O3)c2C1]

[1,1'-Bis(diphenylphosphino)ferrocene]dichloropalladium(II) (0.586 g, 0.801 mmol) was added in one portion to a degassed mixture of tert-butyl 8-bromo-6-(difluoromethyl)-3,4-dihydroisoquinoline-2(1H)-carboxylate (5.8 g, 16.01 mmol), Bis(pinacolato)diboron (8.13 g, 32.0 mmol) and potassium acetate (6.29 g, 64.1 mmol) in Dioxane (60 ml) and the reaction mixture was heated to 100° C. for 2 h. The mixture was then cooled to 25° C. and filtered through a celite bed, washed with ethyl acetate (25 ml). The filtrate was concentrated in vacuo to give 6.8 g of a crude compound. This crude residue was purified by combiflash ($R_f$200, Teledyne/Isco) instrument onto a Redisep® $R_f$ column with gradient elution (0 to 5%) of ethyl acetate in petroleum ether to afford the title compound (6.5 g, 99%) as an off white solid. $^1$H NMR (400 MHz, Chloroform-d) δ 7.81 (s, 1H), 7.38 (s, 1H), 6.62 (t, J=56.5 Hz, 1H), 4.91 (s, 2H), 3.66 (t, J=6.0 Hz, 2H), 2.91 (t, J=6.0 Hz, 2H), 1.37 (s, 9H), 1.28 (s, 12H); LCMS m/z=410.23 (M+1; 20%).

(2-(tert-Butoxycarbonyl)-6-(difluoromethyl)-1,2,3,4-tetrahydroisoquinolin-8-yl)boronic Acid

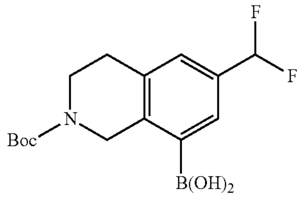 [SMILES: CC(C)(C)OC(=O)N1CCc2cc(C(F)F)cc(B(O)O)c2C1]

Sodium periodate (1.787 g, 8.36 mmol) was added to a mixture of tert-butyl 6-(difluoromethyl)-8-(4,4,5,5-tetramethyl-1,3,2-dioxaborolan-2-yl)-3,4-dihydroisoquinoline-2(1H)-carboxylate (1.14 g, 2.79 mmol) in water (2.5 ml) and acetone (12.50 ml) at 25° C. The resulting mixture was stirred at 25° C. for 1 h. 1N aqueous HCl (2.79 ml, 2.79 mmol) was added and stirred the reaction mixture for an additional 4 h. The reaction mixture was diluted with ethyl acetate (50 ml) and washed with water (50 ml). Layers were separated, the organic layer was washed with brine (50 ml) and dried over anhydrous sodium sulphate. The organic layer was filtered and concentrated in vacuo to give 0.8 g of a crude compound. This crude residue was purified by combiflash ($R_f$200, Teledyne/Isco) instrument onto a Redisep® $R_f$ column with gradient elution (0 to 10%) of methanol in dichloromethane to afford the title compound (0.61 g, 66.9%) as an off-white solid. $^1$H NMR (400 MHz, DMSO-d6) δ 8.29 (s, 2H), 7.56 (s, 1H), 7.35 (s, 1H), 6.97 (t, J=56.0 Hz, 1H), 4.71 (s, 2H), 3.53 (t, J=6.1 Hz, 2H), 2.84 (t, J=6.0 Hz, 2H), 1.42 (s, 9H). LCMS m/z=328.34 (M+1; 10%).

tert-Butyl 6-(difluoromethyl)-8-hydroxy-3,4-dihydroisoquinoline-2(1H)-carboxylate

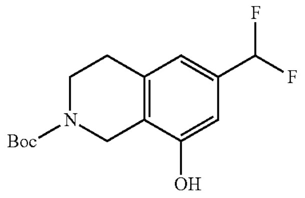 [SMILES: CC(C)(C)OC(=O)N1CCc2cc(C(F)F)cc(O)c2C1]

To a mixture of (2-(tert-butoxycarbonyl)-6-(difluoromethyl)-1,2,3,4-tetrahydroisoquinolin-8-yl)boronic acid (1.5 g, 4.59 mmol) in aq. citric acid solution (36 ml, 0.459 mmol) was added hydrogen peroxide (0.468 ml, 4.59 mmol) at 25° C. and stirred for 3 h. The reaction mixture was diluted with ethyl acetate (50 ml) and washed with water (50 ml). Layers were separated, the organic layer was washed with brine (50 ml) and dried over anhydrous sodium sulphate. The organic layer was filtered and concentrated in vacuo to give 1.2 g of a crude compound. This crude residue was purified by combiflash ($R_f$200, Teledyne/Isco) instrument onto a Redisep® $R_f$ column with gradient elution (0 to 20%) of methanol in dichloromethane to afford the title compound (0.92 g, 67%) as an off-white solid. $^1$H NMR (400 MHz, Chloroform-d) δ 6.82 (s, 1H), 6.77 (s, 1H), 6.53 (t, J=56.6 Hz, 1H), 4.59 (s, 2H), 3.67 (t, J=5.9 Hz, 2H), 2.84 (t, J=5.9 Hz, 2H), 1.53 (s, 9H).

8-Bromo-5-fluoroisoquinoline

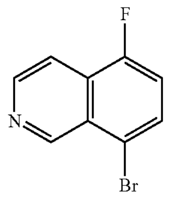 [SMILES: Fc1ccc(Br)c2cnccc12]

The title compound was prepared by following same reaction protocol as described in WO2018/167800 A1.

8-Bromo-5-fluoroisoquinoline-6-carbaldehyde

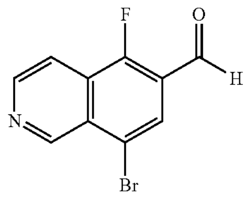 [SMILES: O=Cc1cc(Br)c2cnccc2c1F]

To a stirred solution of 8-bromo-5-fluoroisoquinoline (1.7 g, 7.52 mmol) in THF (15 ml) was added LDA (2 M in THF/heptane/ethylbenzene) (5.64 ml, 11.28 mmol) at −78° C. and stirred for 1 h. DMF (1.747 ml, 22.56 mmol) was added at −78° C. and stirred for 30 min. The resulting mixture was quenched with ice water and allowed to warm to room temperature. The reaction mixture was diluted with ethyl acetate (20 ml) and washed with water (20 ml). Layers were separated, and the organic layer was washed with brine (20 ml) and dried over anhydrous $Na_2SO_4$. The organic layer was filtered and concentrated in vacuo to give 1 g of a crude compound. This residue was purified by combiflash ($R_f$200, Teledyne/Isco) instrument onto a Redisep® $R_f$ column with gradient elution (0 to 10%) of ethyl acetate in petroleum ether to afford (0.467 g, 24.44%) of the title compound. LCMS m/z=254.14 (M+; 90%).

8-Bromo-6-(difluoromethyl)-5-fluoroisoquinoline

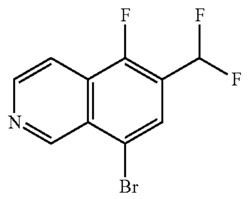 [SMILES: Fc1c(C(F)F)cc(Br)c2cnccc12]

To a stirred solution of 8-bromo-5-fluoroisoquinoline-6-carbaldehyde (233 mg, 0.917 mmol) in DCM (6 ml) was added DAST (0.606 ml, 4.59 mmol) at 0° C. and stirred the reaction mixture for 15 min. The resulting mixture was allowed to warm to room temperature and stirred for 16 h. The resulting mixture was diluted with dichloromethane (10 ml) and quenched with cold saturated aqueous $NaHCO_3$ solution (20 ml). Stirred the reaction mixture at room temperature for 20 mins. Layers were separated, and the organic layer was washed with brine (20 ml) and dried over anhydrous $Na_2SO_4$. The organic layer was filtered and concentrated in vacuo to give 0.8 g of a crude compound. This residue was purified by combiflash ($R_f$200, Teledyne/Isco) instrument onto a Redisep® $R_f$ column with gradient elution (0 to 10%) of ethyl acetate in petroleum ether to afford (0.166 g, 65.6%) of the title compound. LCMS m/z=276.02 (M+; 100%).

(3aS,4S,6aR)-6-Formyl-2,2-dimethyl-3a,6a-dihydro-4H-cyclopenta[d][1,3]dioxol-4-yl Acetate

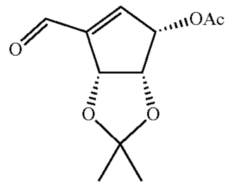 [SMILES: CC(=O)O[C@H]1C=C(C=O)[C@H]2OC(C)(C)O[C@@H]12]

To a stirred solution of (3aS,4S,6aR)-6-(hydroxymethyl)-2,2-dimethyl-3a,6a-dihydro-4H-cyclopenta[d][1,3]dioxol-4-yl acetate, which was synthesized as described in Bioorganic and medicinal Chemistry, 1996, 4(7), 1077-1088, (18 g, 79 mmol) in DCM (500 ml) at 0° C. was added Dess-Martin Periodinane (66.9 g, 158 mmol) portion wise under $N_2$ atmosphere. The reaction mixture was slowly warmed to 25° C. and stirred for 2 h. The reaction mixture was diluted with dichloromethane (200 ml) and washed with water (200 ml). Layers were separated, the organic layer was washed with brine (100 ml) and dried over anhydrous sodium sulphate. The organic layer was filtered and concentrated in vacuo to give 29 g of a crude compound. This crude residue was purified by combiflash ($R_f$200, Teledyne/Isco) instrument onto a Redisep® $R_f$ column with gradient elution (0 to 35%) of ethyl acetate in petroleum ether to afford the title compound (15.5 g, 87%) as a pale yellow liquid. $^1H$ NMR (400 MHz, Chloroform-d) δ 9.92 (s, 1H), 6.78 (d, J=2.1 Hz, 1H), 5.55 (dd, J=5.6, 2.1 Hz, 1H), 5.28 (d, J=5.6 Hz, 1H), 5.02 (t, J=5.6 Hz, 1H), 2.19 (s, 3H), 1.41 (s, 6H).

(3aS,4S,6aR)-2,2-Dimethyl-6-vinyl-3a,6a-dihydro-4H-cyclopenta[d][1,3]dioxol-4-yl Acetate

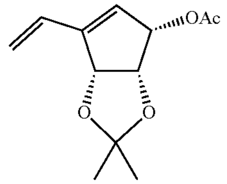 [SMILES: C=CC1=C[C@H](OC(C)=O)[C@@H]2OC(C)(C)O[C@H]12]

To a stirred solution of methyltriphenylphosphonium bromide (6.16 g, 17.24 mmol) in dry THF (50 ml) was added n-BuLi (2.5 M in hexane; 6.37 ml, 15.91 mmol) dropwise at −15° C. and stirred for 30 min at same temperature. The solution of (3aS,4S,6aR)-6-formyl-2,2-dimethyl-3a,6a-dihydro-4H-cyclopenta[d][1,3]dioxol-4-yl acetate (3.0 g, 13.26 mmol) in dry THF (15 ml) was added dropwise in above reaction mixture at −15° C. and slowly allowed to attain 0° C. to 10° C. within 1 h. The reaction mixture quenched with saturated solution of ammonium chloride (50 mL) diluted with in ethyl acetate (70 mL). Layers were separated, the combined organic layer was washed with brine (30 mL), dried over anhydrous $Na_2SO_4$, filtered and concentrated in vacuo to give 4.5 g of a crude compound. This residue was purified by combiflash ($R_f$200, Teledyne/Isco) instrument onto a Redisep® $R_f$ column with gradient elution (4-6%) of ethyl acetate in petroleum ether to afford the title compound as a colourless liquid. $^1$H NMR (400 MHz, Chloroform-d) δ 6.49 (dd, J=17.7, 10.8 Hz, 1H), 5.76-5.63 (m, 2H), 5.45-5.35 (m, 2H), 5.18 (d, J=5.8 Hz, 1H), 4.93 (t, J=5.8 Hz, 1H), 2.14 (s, 3H), 1.44-1.39 (m, 6H).

7-((3aS,4R,6aR)-6-(((tert-Butyldiphenylsilyl)oxy)methyl)-2,2-dimethyl-3a,6a-dihydro-4H-cyclopenta[d][1,3]dioxol-4-yl)-4-chloro-2-methyl-7H-pyrrolo[2,3-d]pyrimidine

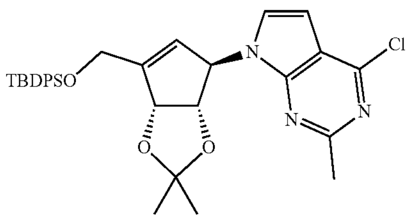

To a stirred solution of (3aS,4S,6aR)-6-(((tert-butyldiphenylsilyl)oxy)methyl)-2,2-dimethyl-3a,6a-dihydro-4H-cyclopenta[d][1,3]dioxol-4-ol (0.1 g, 0.236 mmol), which was synthesized as described in Kenneth A. Jacobson et. al; Purinergic Signaling (2015) 11:371-387, in THF (5 ml) was added commercially available 4-chloro-2-methyl-7H-pyrrolo[2,3-d]pyrimidine (0.079 g, 0.471 mmol), triphenylphosphine (0.247 g, 0.942 mmol) at 0° C. DIAD (0.183 ml, 0.942 mmol) was added and stirred for 10 min. Warmed the reaction to 25° C. and stirred for 12 h. Volatiles were removed in vacuo and the crude residue was purified by combiflash ($R_f$200, Teledyne/Isco) instrument onto a Redisep® $R_f$ column with gradient elution (0 to 10%) of ethyl acetate in petroleum ether to afford the title compound (0.1 g, 73.9%) as a colourless oil. $^1$H NMR (400 MHz, DMSO-d6) δ 7.65 (ddd, J=8.1, 6.7, 1.5 Hz, 4H), 7.50-7.39 (m, 6H), 7.33 (d, J=3.7 Hz, 1H), 6.65 (d, J=3.6 Hz, 1H), 5.77 (s, 2H), 5.41 (d, J=5.6 Hz, 1H), 4.65 (d, J=5.6 Hz, 1H), 4.51 (d, J=15.8 Hz, 1H), 4.39 (d, J=15.8 Hz, 1H), 2.64 (s, 3H), 1.34 (s, 3H), 1.25 (s, 3H), 1.02 (s, 9H); LCMS m/z=574.08 (M+; 100%).

((3aS,4R,6aR)-4-(4-Chloro-2-methyl-7H-pyrrolo[2,3-d]pyrimidin-7-yl)-2,2-dimethyl-3a,6a-dihydro-4H-cyclopenta[d][1,3]dioxol-6-yl)methanol

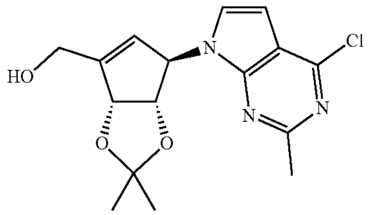 [SMILES: Cc1nc(Cl)c2ccn([C@@H]3C=C(CO)[C@H]4OC(C)(C)O[C@H]43)c2n1]

To a stirred solution of 7-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-4-chloro-2-methyl-7H-pyrrolo[2,3-d]pyrimidine (2.1 g, 3.66 mmol) in THF (20 ml) was added TBAF (5.12 ml, 5.12 mmol) slowly and stirred the reaction mixture at 25° C. for 15 h. Volatiles were removed in vacuo and the crude residue was purified by combiflash ($R_f$200, Teledyne/Isco) instrument onto a Redisep® $R_f$ column with gradient elution (0 to 30%) of ethyl acetate in petroleum ether to afford the title compound (1 g, 81%) as a colourless oil. $^1$H NMR (400 MHz, DMSO-d6) δ 7.41 (d, J=3.7 Hz, 1H), 6.63 (d, J=3.6 Hz, 1H), 5.75-5.70 (m, 1H), 5.65 (d, J=2.4 Hz, 1H), 5.37 (d, J=5.7 Hz, 1H), 5.09 (t, J=5.6 Hz, 1H), 4.58 (d, J=5.7 Hz, 1H), 4.17 (dd, J=5.1, 2.5 Hz, 2H), 2.67 (s, 3H), 1.40 (s, 3H), 1.28 (s, 3H); LCMS m/z=336.28 (M+1; 30%).

4-Chloro-7-((3aS,4R,6aR)-6-(iodomethyl)-2,2-dimethyl-3a,6a-dihydro-4H-cyclopenta[d][1,3]dioxol-4-yl)-2-methyl-7H-pyrrolo[2,3-d]pyrimidine

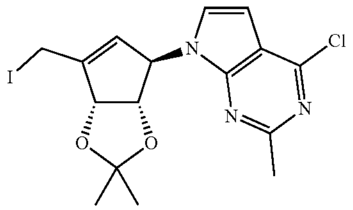 [SMILES: Cc1nc(Cl)c2ccn([C@@H]3C=C(CI)[C@H]4OC(C)(C)O[C@H]43)c2n1]

To a stirred solution of imidazole (0.223 g, 3.28 mmol) and triphenylphosphine (0.508 g, 1.936 mmol) in DCM (10 ml) was added iodine (0.491 g, 1.936 mmol) slowly at 0° C. A solution of ((3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxol-6-yl)methanol (0.5 g, 1.489 mmol) dissolved in DCM (10 ml) was added thereto and stirred for 10 min. The resulting mixture was stirred for 3 h at 25° C. The reaction mixture was diluted with dichloromethane (50 ml) and washed with water (50 ml). Layers were separated, the organic layer was washed with brine (50 ml) and dried over anhydrous sodium sulphate. The organic layer was filtered and concentrated in vacuo to give 0.6 g of a crude compound. This crude residue was purified by combiflash ($R_f$200, Teledyne/Isco) instrument onto a Redisep® $R_f$ column with gradient elution (0 to 6%) of ethyl acetate in petroleum ether to afford the title compound (0.34 g, 51.2%) as a light brown oil. LCMS m/z=446 (M+; 100%).

(3aS,4R,6aR)-4-(4-Chloro-2-methyl-7H-pyrrolo[2,3-d]pyrimidin-7-yl)-2,2-dimethyl-3a,6a-dihydro-4H-cyclopenta[d][1,3]dioxole-6-carbaldehyde

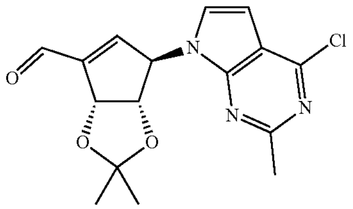 [SMILES: Cc1nc(Cl)c2ccn([C@@H]3C=C(C=O)[C@H]4OC(C)(C)O[C@H]43)c2n1]

To a cold solution (0° C.) of ((3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxol-6-yl)methanol (0.9 g, 2.68 mmol) in DCM (50 ml) was added Dess-Martin Periodinane (5.68 g, 13.40 mmol) portion-wise and stirred the reaction mixture for 10 min. The resulting mixture was stirred for 4 h at 25° C. Volatiles were removed in vacuo and the crude residue was purified by combiflash ($R_f$200, Teledyne/Isco) instrument onto a Redisep® $R_f$ column with gradient elution (0 to 20%) of ethyl acetate in petroleum ether to afford the title compound (0.75 g, 84%) as a colourless oil. $^1$H NMR (400 MHz, DMSO-d6) δ 9.90 (s, 1H), 7.58 (d, J=3.7 Hz, 1H), 7.05 (dd, J=2.6, 0.9 Hz, 1H), 6.66 (d, J=3.7 Hz, 1H), 6.0-5.96 (m, 1H), 5.64 (dd, J=5.9, 1.5 Hz, 1H), 4.81-4.77 (m, 1H), 2.65 (s, 3H), 1.40 (s, 3H), 1.29 (s, 3H); LCMS m/z=334.34 (M+1; 100%).

4-Chloro-7-((3aS,4R,6aR)-2,2-dimethyl-6-vinyl-3a,6a-dihydro-4H-cyclopenta[d][1,3]dioxol-4-yl)-2-methyl-7H-pyrrolo[2,3-d]pyrimidine

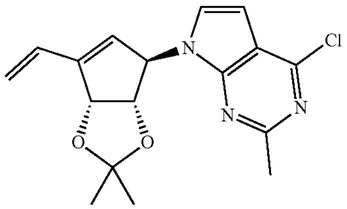 [SMILES: C=CC1=C[C@@H](n2ccc3c(Cl)nc(C)nc32)[C@@H]2OC(C)(C)O[C@H]12]

To a suspension of methyltriphenyl phosphonium bromide (0.783 g, 2.193 mmol) in THF (6 ml) was added KHMDS (2.193 ml, 2.193 mmol) slowly at 0° C. After 5 min, a solution of (3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxole-6-carbaldehyde (0.61 g, 1.828 mmol) in THF (3 ml) was added slowly and stirred the reaction at same temperature for 5 min. The reaction mixture was diluted with ethyl acetate (5 ml) and washed with water (2 ml). Layers were separated, the organic layer was washed with brine (5 ml) and dried over anhydrous sodium sulphate. The organic layer was filtered and concentrated in vacuo to give 0.36 g of a crude compound. This crude residue was purified by combiflash ($R_f$200, Teledyne/Isco) instrument onto a Redisep® $R_f$ column with gradient elution (0 to 10%) of ethyl acetate in petroleum ether to afford the title compound (0.28 g, 46.2%) as an off white solid. $^1$H NMR (400 MHz, DMSO-d6) δ 7.43 (d, J=3.7 Hz, 1H), 6.65-6.55 (m, 2H), 5.85 (d, J=2.7 Hz, 1H), 5.79 (s, 1H), 5.64 (d, J=1.7 Hz, 1H), 5.63-5.59 (m, 1H), 5.42 (dd, J 10.8, 1.7 Hz, 1H), 4.68 (dd, J=5.9, 1.0 Hz, 1H), 2.66 (s, 3H), 1.39 (s, 3H), 1.32 (s, 3H); LCMS m/z=332.11 (M+1; 100%).

tert-Butyl (tert-butoxycarbonyl)(7-((3aS,4R,6aR)-2,2-dimethyl-6-vinyl-3a,6a-dihydro-4H-cyclopenta[d][1,3]dioxol-4-yl)-4-methyl-7H-pyrrolo[2,3-d]pyrimidin-2-yl)carbamate

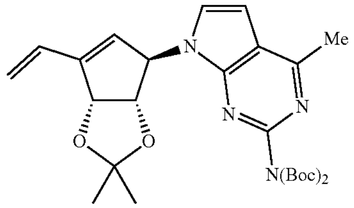

To a solution of (3aS,4S,6aR)-2,2-dimethyl-6-vinyl-3a,6a-dihydro-4H-cyclopenta[d][1,3]dioxol-4-ol (1 g, 5.49 mmol), which was synthesized as described in Organic letters, 2012, 14, 2134-2137, triphenylphosphine (3.6 g, 13.72 mmol), tert-butyl (tert-butoxycarbonyl)(4-methyl-7H-pyrrolo[2,3-d]pyrimidin-2-yl)carbamate (2.103 g, 6.04 mmol), which was synthesized as described in US2016/244475 A1, at 0° C. was added DIAD (2.67 ml, 13.72 mmol) slowly. After stirring for 10 mins, the reaction mixture was stirred at 25° C. for 3 h. Volatiles were removed in vacuo and the crude residue was purified by combiflash ($R_f$200, Teledyne/Isco) instrument onto a Redisep® $R_f$ column with gradient elution (0 to 30%) of ethyl acetate in petroleum ether to afford 2 g of sufficiently pure desired compound. This residue was then purified by reverse phase preparative HPLC (YMC Triart C18 250×50 mm, 10 m) with gradient elution of mobile phase B in mobile phase A (40:60 mobile phase A: mobile phase B to 20:80 mobile phase A: mobile phase B; Mobile Phase A: Water:$CH_3CN$ (95:5, V/V)+0.1% $NH_4OH$, Mobile Phase B: $CH_3CN$:Water (90:10, V/V)+0.1% $NH_4OH$; Wavelength: 220 nm; Flow Rate: 117 ml/min; Run time: 20 min) to afford (0.61 g, 21.68%) of the title compound as an off white solid. $^1$H NMR (400 MHz, DMSO-d6) δ 7.39 (d, J=3.6 Hz, 1H), 6.76 (d, J=3.6 Hz, 1H), 6.61 (dd, J=17.6, 10.8 Hz, 1H), 5.89 (d, J=2.6 Hz, 1H), 5.71 (s, 1H), 5.65-5.55 (m, 2H), 5.45-5.37 (m, 1H), 4.59 (d, J=5.9 Hz, 1H), 2.66 (s, 3H), 1.40 (s, 18H), 1.37 (s, 3H), 1.30 (s, 3H); LCMS m/z=512.44 (M+; 50%).

3-Chloro-7-(2-((3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine

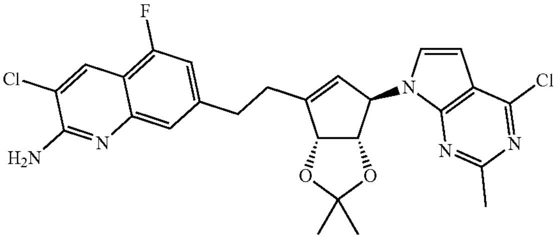 [SMILES: Cc1nc(Cl)c2ccn([C@@H]3C=C(CCc4cc(F)c5cc(Cl)c(N)nc5c4)[C@H]4OC(C)(C)O[C@H]43)c2n1]

4-Chloro-7-((3aS,4R,6aR)-2,2-dimethyl-6-vinyl-3a,6a-dihydro-4H-cyclopenta[d][1,3]dioxol-4-yl)-2-methyl-7H-pyrrolo[2,3-d]pyrimidine (0.28 g, 0.844 mmol) in 9-BBN (6.75 ml, 3.38 mmol) was heated at 70° C. for 2 h under $N_2$ atmosphere. The reaction mixture was cooled to 25° C., then potassium phosphate tribasic (0.896 g, 4.22 mmol) in water (1 ml) was added and stirred for 30 mins. A solution of 7-bromo-3-chloro-5-fluoroquinolin-2-amine (0.256 g, 0.928 mmol) in THF (5 ml) was added, followed by dichloro[1,1'-bis(di-t-butylphosphino)ferrocene]palladium(II) (0.055 g, 0.084 mmol). The resulting mixture was stirred at 70° C. for 3 h. The reaction mixture was diluted with ethyl acetate (10 ml) and washed with water (10 ml). Layers were separated, and the organic layer was washed with brine (10 ml) and dried over anhydrous $Na_2SO_4$. The organic layer was filtered and concentrated in vacuo to give 0.25 g of a crude compound. This residue was purified by combiflash ($R_f$200, Teledyne/Isco) instrument onto a Redisep® $R_f$ column with gradient elution (0 to 20%) of ethyl acetate in petroleum ether to afford the title compound (0.17 g, 38.1%) as an off-white solid. $^1$H NMR (400 MHz, DMSO-d6) δ 8.18 (s, 1H), 7.25 (s, 1H), 7.04 (dd, J=11.0, 1.4 Hz, 1H), 6.97 (s, 2H), 6.92 (d, J=3.7 Hz, 1H), 6.36 (d, J=3.7 Hz, 1H), 5.64 (d, J=3.6 Hz, 1H), 5.49 (s, 1H), 5.38 (d, J=5.6 Hz, 1H), 4.49 (d, J=5.6 Hz, 1H), 3.08-2.94 (m, 2H), 2.71-2.65 (m, 2H), 2.64 (s, 3H), 1.38 (s, 3H), 1.29 (s, 3H); LCMS m/z=528.1 (M+; 100%).

7-(2-((3aS,4R,6aR)-4-(4-Amino-2-methyl-7H-pyrrolo[2,3-d]pyrimidin-7-yl)-2,2-dimethyl-3a,6a-dihydro-4H-cyclopenta[d][1,3]dioxol-6-yl)ethyl)-3-chloro-5-fluoroquinolin-2-amine

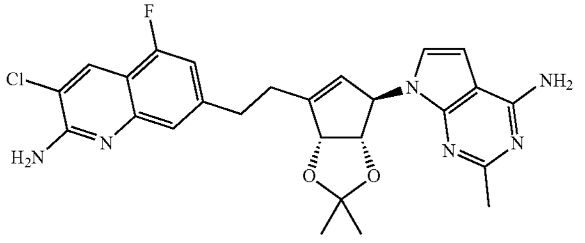 [SMILES: Cc1nc(N)c2ccn([C@@H]3C=C(CCc4cc(F)c5cc(Cl)c(N)nc5c4)[C@H]4OC(C)(C)O[C@H]43)c2n1]

To a mixture of 3-chloro-7-(2-((3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine (0.170 g, 0.322 mmol) in dioxane (1 ml), was added aq. ammonia (2.089 ml, 97 mmol) at 25° C. and stirred the reaction mixture at 120° C. for 16 h in a steel bomb. Volatiles were removed in vacuo and the crude residue was purified by combiflash ($R_f$200, Teledyne/Isco) instrument onto a Redisep® $R_f$ column with gradient elution (0 to 2%) of methanol in dichloromethane to afford the title compound (0.08 g, 48.9%) as a colourless oil. LCMS m/z=509.2 (M+1; 25%).

tert-Butyl (tert-butoxycarbonyl)(7-((3aS,4R,6aR)-6-(2-(6-(difluoromethyl)-5-fluoroisoquinolin-8-yl)ethyl)-2,2-dimethyl-3a,6a-dihydro-4H-cyclopenta[d][1,3]dioxol-4-yl)-4-methyl-7H-pyrrolo[2,3-d]pyrimidin-2-yl)carbamate

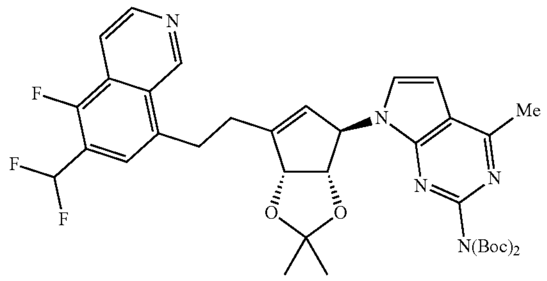

tert-Butyl (tert-butoxycarbonyl)(7-((3aS,4R,6aR)-2,2-dimethyl-6-vinyl-3a,6a-dihydro-4H-cyclopenta[d][1,3]dioxol-4-yl)-4-methyl-7H-pyrrolo[2,3-d]pyrimidin-2-yl)carbamate (0.560 g, 1.092 mmol) in 9-BBN (8.74 ml, 4.37 mmol) was heated at 65° C. for 1.5 h under $N_2$ atmosphere. The reaction mixture was cooled to 25° C., then potassium phosphate tribasic (0.951 g, 5.46 mmol) in water (2 ml) was added and stirred for 30 mins. A solution of 8-bromo-6-(difluoromethyl)-5-fluoroisoquinoline (0.302 g, 1.092 mmol) in THF (7 ml) was added, followed by the addition of $PdCl_2$(dppf) (0.080 g, 0.109 mmol). The resulting mixture was stirred at 65° C. for 4 h. The reaction mixture was diluted with ethyl acetate (15 ml) and washed with water (15 ml). Layers were separated, and the organic layer was washed with brine (10 ml) and dried over anhydrous $Na_2SO_4$. The organic layer was filtered and concentrated in vacuo to give 0.65 g of crude compound. This residue was purified by combiflash ($R_f$200, Teledyne/Isco) instrument onto a Redisep® $R_f$ column with gradient elution (0 to 20%) of ethyl acetate in petroleum ether to afford the title compound (0.35 g, 45.1%) as an off-white solid. LCMS m/z=710.52 (M+1; 100%).

(3aS,4S,6aR)-6-(((2-(Bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl acetate

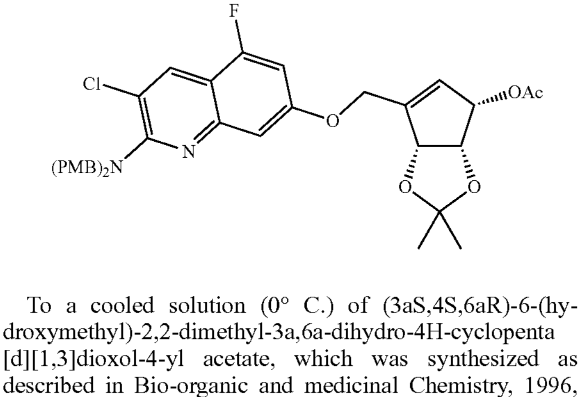

To a cooled solution (0° C.) of (3aS,4S,6aR)-6-(hydroxymethyl)-2,2-dimethyl-3a,6a-dihydro-4H-cyclopenta[d][1,3]dioxol-4-yl acetate, which was synthesized as described in Bio-organic and medicinal Chemistry, 1996, 4(7), 1077-1088, (2 g, 8.76 mmol) in THF (30 ml) was added 2-(bis(4-methoxybenzyl)amino)-3-chloro-5-fluoroquinolin-7-ol (3.97 g, 8.76 mmol), triphenylphosphine (6.89 g, 26.3 mmol) and DIAD (5.11 ml, 26.3 mmol) slowly. After stirring for 30 mins, the reaction mixture was stirred at 25° C. for 15 h. Volatiles were removed in vacuo and the crude residue was purified by combiflash ($R_f$200, Teledyne/Isco) instrument onto a Redisep® $R_f$ column with gradient elution (0 to 30%) of ethyl acetate in petroleum ether to afford the title compound (3.8 g, 65.4%) as an orange liquid. $^1$H NMR (400 MHz, DMSO-$d_6$) δ 8.28 (d, J=0.7 Hz, 1H), 7.28-7.22 (m, 4H), 7.09-6.97 (m, 2H), 6.89-6.83 (m, 4H), 5.88-5.84 (m, 1H), 5.36-5.30 (m, 1H), 5.04 (d, J=5.7 Hz, 1H), 4.91-4.86 (m, 3H), 4.55 (s, 4H), 3.71 (s, 6H), 2.03 (s, 3H), 1.32 (s, 3H), 1.30 (s, 3H); LCMS m/z=663.10 (M+; 100%).

(3aS,4S,6aR)-6-(((2-(Bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-ol

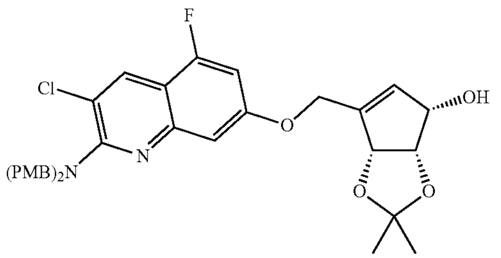

To a stirred suspension of (3aS,4S,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl acetate (3.8 g, 5.73 mmol) in methanol (40 ml) was added $K_2CO_3$ (1.188 g, 8.60 mmol) at 25° C. The resulting mixture was stirred at 25° C. for 1 h under $N_2$ atmosphere. Volatiles were removed in vacuo and the crude residue was purified by combiflash ($R_f$200, Teledyne/Isco) instrument onto a Redisep® $R_f$ column with gradient elution (0 to 50%) of ethyl acetate in petroleum ether to afford the title compound (2.6 g, 73.1%) as an off white solid. LCMS m/z=620.96 (M+; 100%).

tert-Butyl (7-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-2-methyl-7H-pyrrolo[2,3-d]pyrimidin-4-yl)(tert-butoxycarbonyl)carbamate

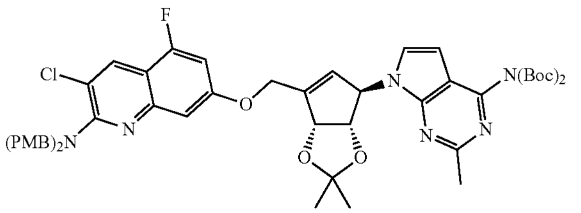

To a stirred solution of (3aS,4S,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-ol (0.35 g, 0.564 mmol) in THF (15 ml) was added tert-Butyl (tert-butoxycarbonyl)(2-methyl-7H-pyrrolo[2,3-d]pyrimidin-4-yl)carbamate (0.393 g, 1.127 mmol), triphenylphosphine (0.443 g, 1.691 mmol) at 0° C. DEAD (0.268 ml, 1.691 mmol) was added slowly and stirred for 30 min. The resulting mixture was stirred at 25° C. for 16 h. Volatiles were removed in vacuo and the crude residue was purified by combiflash ($R_f$200, Teledyne/Isco) instrument onto a Redisep® $R_f$ column with gradient elution (0 to 50%) of ethyl acetate in petroleum ether to afford the title compound (0.2 g, 37.3%) as an off white solid. $^1$H NMR (400 MHz, DMSO-$d_6$) δ 8.29 (s, 1H), 7.27-7.24 (m, 4H), 7.10 (d, J=2.3 Hz, 1H), 7.04 (dd, J=11.3, 2.2 Hz, 1H), 6.90-6.82 (m, 4H), 6.27 (d, J=3.7 Hz, 1H), 5.85 (s, 1H), 5.78 (s, 1H), 5.52 (d, J=5.6 Hz, 1H), 5.07-4.91 (m, 3H), 4.65 (d, J=5.7 Hz, 1H), 4.55 (s, 4H), 3.71 (s, 6H), 2.00 (s, 3H), 1.44 (s, 3H), 1.41 (s, 18H), 1.31 (s, 3H); LCMS m/z=951.20 (M+; 100%).

tert-Butyl (7-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-4-methyl-7H-pyrrolo[2,3-d]pyrimidin-2-yl)(tert-butoxycarbonyl)carbamate

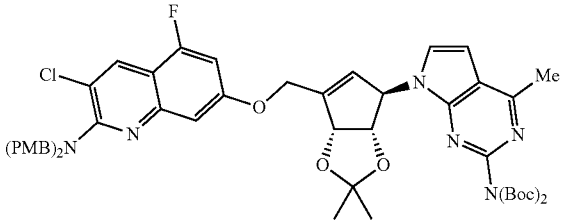

To a stirred solution of (3aS,4S,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-ol (0.400 g, 0.644 mmol) in THF (15 ml), was added tert-butyl (tert-butoxycarbonyl)(4-methyl-7H-pyrrolo[2,3-d]pyrimidin-2-yl)carbamate (0.449 g, 1.288 mmol), which was synthesized as described in US 2016/244475 A1, triphenylphosphine (0.507 g, 1.932 mmol) at 0° C. DEAD (0.306 ml, 1.932 mmol) was then added slowly and stirred for 30 min. The resulting mixture was stirred at 25° C. for 16 h. Volatiles were removed in vacuo and the crude residue was purified by combiflash ($R_f$200, Teledyne/Isco) instrument onto a Redisep® $R_f$ column with gradient elution (0 to 18%) of ethyl acetate in petroleum ether to afford the title compound (0.48 g, 78%) as an off white solid. $^1$H NMR (400 MHz, Chloroform-d) δ 8.19 (s, 1H), 7.28-7.24 (m, 4H), 7.05-7.00 (m, 2H), 6.91-6.83 (m, 4H), 6.77 (dd, J=11.0, 2.3 Hz, 1H), 6.50 (d, J=3.6 Hz, 1H), 5.92 (s, 1H), 5.84 (d, J=2.6 Hz, 1H), 5.46 (d, J=5.6 Hz, 1H), 4.96-4.88 (m, 2H), 4.65 (d, J=5.6 Hz, 1H), 4.62 (s, 4H), 3.81 (s, 6H), 2.72 (s, 3H), 1.52 (s, 3H), 1.46 (s, 18H), 1.36 (s, 3H); LCMS m/z=951.20 (M+; 100%).

(3aS,4S,6aR)-6-(((2-(Bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl acetate

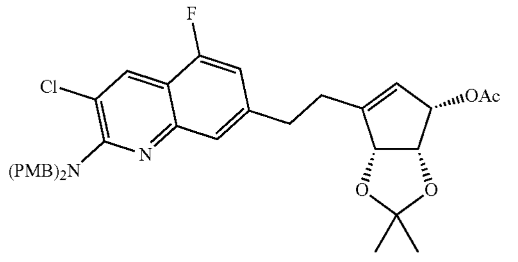

To a stirred solution of (3aS,4S,6aR)-2,2-dimethyl-6-vinyl-3a,6a-dihydro-4H-cyclopenta[d][1,3]dioxol-4-yl acetate (2.000 g, 8.92 mmol) in THF (20 ml) was added 0.5 M 9-BBN (71.3 ml, 35.7 mmol) at 25° C. The resulting mixture was heated at 75° C. for 1.5 h. The reaction mixture was cooled to 25° C., then potassium phosphate tribasic (9.47 g, 44.6 mmol) in water (15 ml) was added and stirred for 20 mins. 7-Bromo-3-chloro-5-fluoro-N,N-bis(4-methoxybenzyl)quinolin-2-amine (3.68 g, 7.13 mmol) and [1,1'-Bis(di-tert-butylphosphino)ferrocene]dichloropalladium(II) (0.291 g, 0.446 mmol) was added at 25° C. and stirred the resulting mixture for 2 h. The reaction mixture was quenched with water (100 ml) and extracted with ethyl acetate (300 ml). Layers were separated, and the organic layer was washed with brine (100 ml) and dried over anhydrous $Na_2SO_4$. The organic layer was filtered and concentrated in vacuo to give 0.25 g of a crude compound. This residue was purified by combiflash ($R_f$200, Teledyne/Isco) instrument onto a Redisep® $R_f$ column with gradient elution (0 to 30%) of ethyl acetate in petroleum ether to afford the title compound (1.7 g, 28.8%) as a colourless semisolid solid. $^1$H NMR (400 MHz, Chloroform-d) δ 8.25 (d, J=0.8 Hz, 1H), 7.42 (s, 1H), 7.29 (d, J=8.6 Hz, 4H), 6.91 (dd, J=10.5, 1.5 Hz, 1H), 6.86 (d, J=8.6, Hz, 4H), 5.55 (q, J=1.7 Hz, 1H), 5.39-5.34 (m, 1H), 4.96-4.88 (m, 2H), 4.60 (s, 4H), 3.81 (s, 6H), 3.05-2.95 (m, 2H), 2.74-2.54 (m, 2H), 2.14 (s, 3H), 1.42 (d, J=7.2 Hz, 6H). LCMS m/z=661.10 (M+; 100%); LCMS m/z=661.22 (M+; 30%).

(3aS,4S,6aR)-6-(2-(2-(Bis(4-methoxybenzyl)amino)-3-chloro-5-fluoroquinolin-7-yl)ethyl)-2,2-dimethyl-3a,6a-dihydro-4H-cyclopenta[d][1,3]dioxol-4-ol

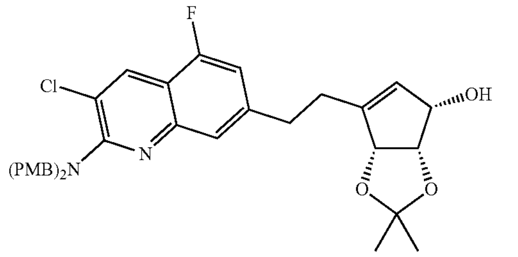

To a stirred solution of (3aS,4S,6aR)-6-(2-(2-(bis(4-methoxybenzyl)amino)-3-chloro-5-fluoroquinolin-7-yl)ethyl)-2,2-dimethyl-3a,6a-dihydro-4H-cyclopenta[d][1,3]dioxol-4-yl acetate (3.4 g, 5.14 mmol) in methanol (60 ml) was added $K_2CO_3$ (1.066 g, 7.71 mmol) at 25° C. The resulting mixture was stirred at 25° C. for 1 h under $N_2$ atmosphere. The reaction mixture quenched with water (100 mL) and extracted with ethyl acetate (300 mL). Layers were separated, the combined organic layer was washed with brine (100 mL), dried over anhydrous $Na_2SO_4$, filtered and concentrated in vacuo to give 4.1 g of a crude compound. This residue was purified by combiflash ($R_f$200, Teledyne/Isco) instrument onto a Redisep® $R_f$ column with gradient elution (0-35%) of ethyl acetate in petroleum ether to afford the title compound (2.75 g, 86%) as a colourless semisolid. $^1$H NMR (400 MHz, Chloroform-d) δ 8.24 (d, J=0.8 Hz, 1H), 7.42 (s, 1H), 7.32-7.27 (m, 4H), 6.91 (dd, J=10.5, 1.5 Hz, 1H), 6.88-6.83 (m, 4H), 5.61-5.52 (m, 1H), 4.90 (d, J=5.6 Hz, 1H), 4.60 (s, 4H), 4.53 (t, J=8.1 Hz, 1H), 3.81 (s, 6H), 3.04-2.91 (m, 2H), 2.64-2.47 (m, 2H), 1.44 (d, J=3.8 Hz, 6H); LCMS m/z=619.09 (M+; 100%).

tert-Butyl (7-((3aS,4R,6aR)-6-(2-(2-(bis(4-methoxybenzyl)amino)-3-chloro-5-fluoroquinolin-7-yl)ethyl)-2,2-dimethyl-3a,6a-dihydro-4H-cyclopenta[d][1,3]dioxol-4-yl)-4-methyl-7H-pyrrolo[2,3-d]pyrimidin-2-yl)(tert-butoxycarbonyl)carbamate

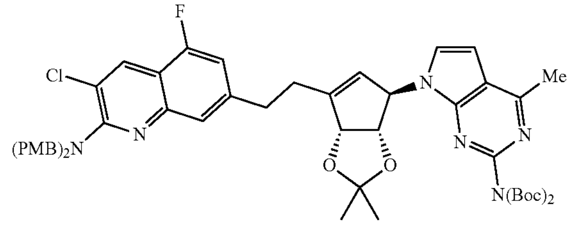

To a stirred solution of (3aS,4S,6aR)-6-(2-(2-(Bis(4-methoxybenzyl)amino)-3-chloro-5-fluoroquinolin-7-yl)ethyl)-2,2-dimethyl-3a,6a-dihydro-4H-cyclopenta[d][1,3]dioxol-4-ol (2.70 g, 4.36 mmol) in THF (50 ml) was added tert-butyl (tert-butoxycarbonyl)(4-methyl-7H-pyrrolo[2,3-d]pyrimidin-2-yl)carbamate (2.279 g, 6.54 mmol), which was synthesized as described in US2016/244475 A1, triphenylphosphine (3.43 g, 13.08 mmol) at 0° C. DEAD (2.071 ml, 13.08 mmol) was then added slowly and stirred for 30 min. The resulting mixture was stirred at 25° C. for 48 h. The reaction mixture was diluted with ethyl acetate 300 ml) and washed with water (100 ml). Layers were separated, and the organic layer was washed with brine (10 ml) and dried over anhydrous $Na_2SO_4$. The organic layer was filtered and concentrated in vacuo to give 11 g of a crude compound. This residue was purified by reverse phase preparative HPLC to afford the title compound (1.15 g, 27.8%) as an off-white solid. $^1$H NMR (400 MHz, Chloroform-d) δ 8.28 (d, J=0.8 Hz, 1H), 7.50 (s, 1H), 7.34-7.24 (m, 6H), 6.96 (dd, J=10.5, 1.4 Hz, 1H), 6.87-6.80 (m, 4H), 6.68 (d, J=3.6 Hz, 1H), 6.34 (d, J=3.6 Hz, 1H), 5.74 (s, 1H), 5.54-5.47 (m, 1H), 5.30 (d, J=5.6 Hz, 1H), 4.63 (s, 4H), 4.51 (d, J=5.6 Hz, 1H), 3.78 (s, 6H), 3.17-3.02 (m, 2H), 2.73 (s, 3H), 1.48 (s, 3H), 1.46 (s, 18H), 1.35 (s, 3H); LCMS m/z=949.20 (M+; 20%).

tert-Butyl 8-(((3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-3,4-dihydroisoquinoline-2(1H)-carboxylate

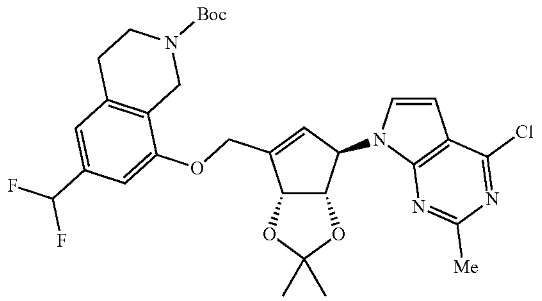 [SMILES: Cc1nc(Cl)c2ccn([C@@H]3C=C(COc4cc(C(F)F)cc5c4CN(C(=O)OC(C)(C)C)CC5)[C@H]4OC(C)(C)O[C@H]43)c2n1]

To a solution of tert-butyl 6-(difluoromethyl)-8-hydroxy-3,4-dihydroisoquinoline-2(1H)-carboxylate (0.054 g, 0.179 mmol) in DMF (2 ml) was added $Cs_2CO_3$ (0.066 g, 0.202 mmol) at 25° C. and stirred for 30 min. 4-Chloro-7-((3aS,4R,6aR)-6-(iodomethyl)-2,2-dimethyl-3a,6a-dihydro-4H-cyclopenta[d][1,3]dioxol-4-yl)-2-methyl-7H-pyrrolo[2,3-d]pyrimidine (0.100 g, 0.224 mmol) dissolved in DMF (2 ml) was slowly at 0° C. and stirred for 3 h. The reaction mixture was diluted with ethyl acetate (25 ml) and washed with water (25 ml). Layers were separated, and the organic layer was washed with brine (10 ml) and dried over anhydrous $Na_2SO_4$. The organic layer was filtered and concentrated in vacuo to give 0.11 g of crude compound. This residue was purified by combiflash ($R_f$200, Teledyne/Isco) instrument onto a Redisep® $R_f$ column with gradient elution (0-30%) of ethyl acetate in petroleum ether to afford the title compound (0.1 g, 72.2%) as an off-white solid. $^1H$ NMR (400 MHz, Chloroform-d) δ 7.03 (s, 1H), 6.91 (d, J=5.5 Hz, 2H), 6.73-6.43 (m, 2H), 5.87 (s, 2H), 5.50 (d, J=5.5 Hz, 1H), 4.97-4.85 (m, 2H), 4.73 (d, J=5.7 Hz, 1H), 4.59 (s, 2H), 3.65 (s, 2H), 2.89-2.81 (m, 5H), 1.54 (s, 3H), 1.48 (s, 9H), 1.40 (s, 3H); LCMS m/z=616.96 (M+; 10%).

tert-Butyl 8-(((3aS,4R,6aR)-4-(4-amino-2-methyl-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-3,4-dihydroisoquinoline-2(1H)-carboxylate

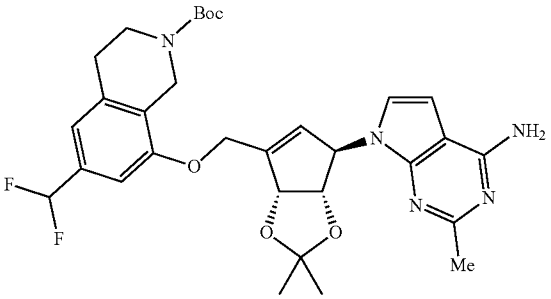 [SMILES: Cc1nc(N)c2ccn([C@@H]3C=C(COc4cc(C(F)F)cc5c4CN(C(=O)OC(C)(C)C)CC5)[C@H]4OC(C)(C)O[C@H]43)c2n1]

To a mixture of tert-butyl 8-(((3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-3,4-dihydroisoquinoline-2(1H)-carboxylate (0.100 g, 0.162 mmol) in dioxane (1 ml) was added aq. ammonia (0.701 ml, 32.4 mmol) at 25° C. and stirred the reaction mixture at 120° C. for 16 h in a steel bomb. Volatiles were removed in vacuo and the crude residue was purified by combiflash ($R_f$200, Teledyne/Isco) instrument onto a Redisep® $R_f$ column with gradient elution (0 to 2%) of methanol in dichloromethane to afford the title compound (0.045 g, 46.5%) as a colourless oil. LCMS m/z=598.06 (M+; 100%).

tert-Butyl 8-(2-((3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-3,4-dihydroisoquinoline-2(1H)-carboxylate

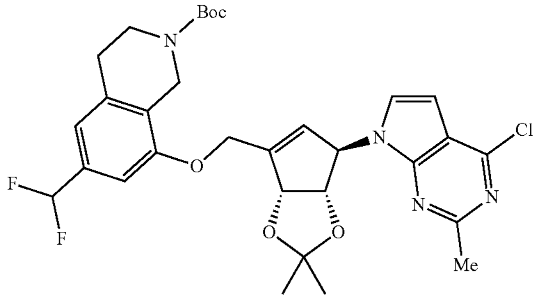 [SMILES: Cc1nc(Cl)c2ccn([C@@H]3C=C(COc4cc(C(F)F)cc5c4CN(C(=O)OC(C)(C)C)CC5)[C@H]4OC(C)(C)O[C@H]43)c2n1]

4-Chloro-7-((3aS,4R,6aR)-2,2-dimethyl-6-vinyl-3a,6a-dihydro-4H-cyclopenta[d][1,3]dioxol-4-yl)-2-methyl-7H-pyrrolo[2,3-d]pyrimidine (0.100 g, 0.301 mmol) in 9-BBN (1.808 ml, 0.904 mmol) was heated at 60° C. for 1 h under $N_2$ atmosphere. The reaction mixture was cooled to 25° C., then potassium phosphate tribasic (0.192 g, 0.904 mmol) in water (0.2 ml) was added and stirred for 15 mins. A solution of tert-butyl 8-bromo-6-(difluoromethyl)-3,4-dihydroisoquinoline-2(1H)-carboxylate (0.109 g, 0.301 mmol) in THF (1 ml) was added, followed by $PdCl_2(dppf)-CH_2Cl_2$ adduct (8.61 mg, 10.55 μmol). The resulting mixture was stirred at 60° C. for 4 h. The reaction mixture was diluted with ethyl acetate (10 ml) and washed with water (10 ml). Layers were separated, and the organic layer was washed with brine (10 ml) and dried over anhydrous $Na_2SO_4$. The organic layer was filtered and concentrated in vacuo to give 0.11 g of a crude compound. This residue was purified by combiflash ($R_f$200, Teledyne/Isco) instrument onto a Redisep® $R_f$ column with gradient elution (0 to 20%) of ethyl acetate in petroleum ether to afford the title compound (0.034 g, 18.34%) as an off-white solid. $^1H$ NMR (400 MHz, DMSO-$d_6$) δ 7.34 (s, 1H), 7.23 (d, J=23.4 Hz, 2H), 6.96 (t, J=56.0 Hz, 1H), 6.57 (d, J=3.7 Hz, 1H), 5.69 (s, 1H), 5.59 (d, J=2.4 Hz, 1H), 5.43 (d, J=5.6 Hz, 1H), 4.57 (s, 3H), 3.55 (s, 2H), 2.97-2.78 (m, 4H), 2.66 (s, 3H), 2.60-2.54 (m, 2H), 1.43-1.36 (m, 12H), 1.30 (s, 3H). LCMS m/z=614.95 (M+; 90%).

tert-Butyl 8-(2-((3aS,4R,6aR)-4-(4-amino-2-methyl-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-3,4-dihydroisoquinoline-2(1H)-carboxylate

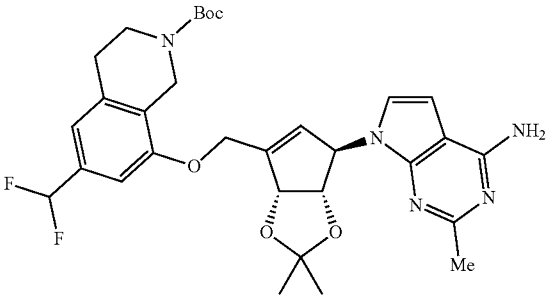 [SMILES: Cc1nc(N)c2ccn([C@@H]3C=C(COc4cc(C(F)F)cc5c4CN(C(=O)OC(C)(C)C)CC5)[C@H]4OC(C)(C)O[C@H]43)c2n1]

To a mixture of tert-butyl 8-(2-((3aS,4R,6aR)-4-(4-chloro-2-methyl-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-3,4-dihydroisoquinoline-2(1H)-carboxylate (0.250 g, 0.406 mmol) in dioxane (2 ml) was added aq. ammonia (1.759 ml, 81 mmol) at 25° C. and stirred the reaction mixture at 120° C. for 16 h in a steel bomb. Volatiles were removed in vacuo and the crude residue was purified by combiflash ($R_f$200, Teledyne/Isco) instrument onto a Redisep® $R_f$ column with gradient elution (0 to 2%) of methanol in dichloromethane to afford the title compound (0.21 g, 87%) as a colourless oil. LCMS m/z=496.3 (M-100; 50%).

tert-Butyl (tert-butoxycarbonyl)(7-((3aS,4R,6aR)-6-(2-(6-(difluoromethyl)-5-fluoro-1,2,3,4-tetrahydroisoquinolin-8-yl)ethyl)-2,2-dimethyl-3a,6a-dihydro-4H-cyclopenta[d][1,3]dioxol-4-yl)-4-methyl-7H-pyrrolo[2,3-d]pyrimidin-2-yl)carbamate

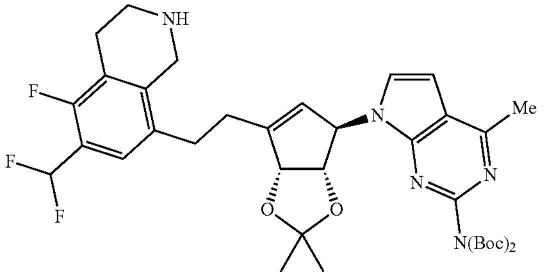

To a stirred solution of tert-butyl (tert-butoxycarbonyl)(7-((3aS,4R,6aR)-6-(2-(6-(difluoromethyl)-5-fluoroisoquinolin-8-yl)ethyl)-2,2-dimethyl-3a,6a-dihydro-4H-cyclopenta[d][1,3]dioxol-4-yl)-4-methyl-7H-pyrrolo[2,3-d]pyrimidin-2-yl)carbamate (0.350 g, 0.493 mmol) in acetic acid (7 ml) was added $NaBH_4$ (0.065 g, 1.726 mmol) portion-wise at 25° C. and stirred for 2 h. Volatiles were removed in vacuo and the residue dissolved in dichloromethane (15 ml) and basified with saturated aqueous $NaHCO_3$. Layers were separated, organic layer was washed with brine (10 ml) and dried over anhydrous $Na_2SO_4$. The organic layer was filtered and concentrated in vacuo to give (0.25 g, 71%) of a crude compound. LCMS m/z=714.52 (M+; 100%).

EXAMPLES

Example-1: (1S,2R,5R)-3-(2-(2-Amino-3-chloro-5-fluoroquinolin-7-yl)ethyl)-5-(2-amino-4-methyl-7H-pyrrolo[2,3-d]pyrimidin-7-yl)cyclopent-3-ene-1,2-diol

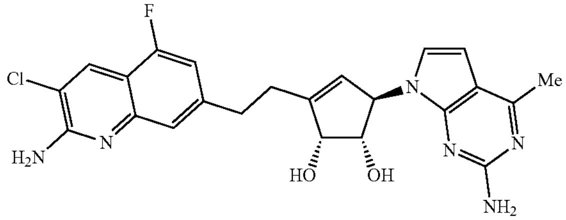 [SMILES: Cc1nc(N)nc2c1ccn2[C@@H]1C=C(CCc2cc(F)c3cc(Cl)c(N)nc3c2)[C@@H](O)[C@H]1O]

A stirred solution of diboc-7-(2-((3aS,4R,6aR)-4-(2-amino-4-methyl-7H-pyrrolo[2,3-d]pyrimidin-7-yl)-2,2-dimethyl-3a,6a-dihydro-4H-cyclopenta[d][1,3]dioxol-6-yl)ethyl)-3-chloro-5-fluoro-N,N-bis(4-methoxybenzyl)quinolin-2-amine (1.10 g, 1.158 mmol) in TFA (8.93 ml, 116 mmol) was stirred at 60° C. for 5 h under $N_2$ atmosphere. Volatiles were removed in vacuo and the residue was diluted with MeOH (15 ml) followed by addition of $K_2CO_3$ (0.801 g, 5.79 mmol). The resulting mixture was stirred at 60° C. for 1.5 h under $N_2$ atmosphere. Volatiles were removed in vacuo and the crude residue was purified by reverse phase preparative HPLC (YMC Triart C18 250×50 mm, 10 μm) with gradient elution of mobile phase B in mobile phase A (100% mobile phase A to 50:50 mobile phase A: mobile phase B; Mobile Phase A: Water:$CH_3CN$ (95:5, V/V)+0.1% $NH_4OH$, Mobile Phase B: $CH_3CN$:Water (90:10, V/V)+0.1% $NH_4OH$; Wavelength: 220 nm; Flow Rate: 117 ml/min; Run time: 20 min) to afford the title compound (0.101 g, 18.59%) as an off white solid. $^1H$ NMR (400 MHz, DMSO-$d_6$) δ 8.18 (s, 1H), 7.21 (s, 1H), 7.00 (dd, J=11.1, 1.4 Hz, 1H), 6.96 (s, 2H), 6.48 (d, J=3.7 Hz, 1H), 6.20 (d, J=3.6 Hz, 1H), 6.07 (s, 2H), 5.40 (d, J=7.2 Hz, 2H), 4.93 (dd, J=25.6, 6.2 Hz, 2H), 4.45 (t, J=6.0 Hz, 1H), 3.98-3.89 (m, 1H), 3.02-2.85 (m, 2H), 2.57-2.52 (m, 2H), 2.38 (s, 3H); LCMS m/z=469.23 (M+; 50%). Examples in table-1 were synthesized by following an analogous reaction protocol as was used for the preparation of (1S,2R,5R)-3-(2-(2-Amino-3-chloro-5-fluoroquinolin-7-yl)ethyl)-5-(2-amino-4-methyl-7H-pyrrolo[2,3-d]pyrimidin-7-yl)cyclopent-3-ene-1,2-diol using the appropriate starting materials.

TABLE 1

| Structure & IUPAC name | Intermediate used | $^{1}H$ NMR & LCMS data |
|---|---|---|
| Example-2: 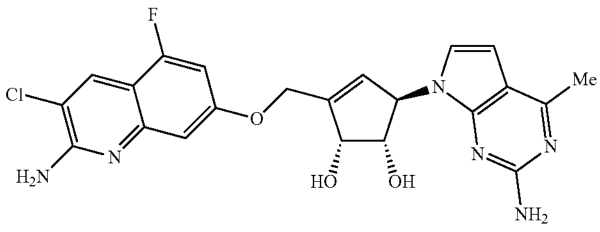 [SMILES: Cc1nc(N)nc2c1ccn2[C@@H]1C=C(COc2cc(F)c3cc(Cl)c(N)nc3c2)[C@@H](O)[C@H]1O] (1S,2R,5R)-3-(((2-Amino-3-chloro-5-fluoroquinolin-7-yl)oxy)methyl)-5-(2-amino-4-methyl-7H-pyrrolo[2,3-d]pyrimidin-7-yl)cyclopent-3-ene-1,2-diol | tert-Butyl(7-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-4-methyl-7H-pyrrolo[2,3-d]pyrimidin-2-yl)(tert-butoxycarbonyl)carbamate | $^{1}H$ NMR (400 MHz, DMSO-$d_6$) δ 8.09 (s, 1H), 6.93 (s, 2H), 6.88-6.78 (m, 3H), 6.37 (d, J = 3.7 Hz, 1H), 6.08 (s, 2H), 5.76 (d, J = 2.0 Hz, 1H), 5.51 (d, J = 5.0 Hz, 1H), 5.15 (d, J = 6.1 Hz, 1H), 5.09 (d, J = 6.6 Hz, 1H), 4.91-4.76 (m, 2H), 4.57 (t, J = 5.8 Hz, 1H), 4.17-4.11 (m, 1H), 2.41 (s, 3H). LCMS m/z = 471.11 (M+; 100%). |
| Example-3: 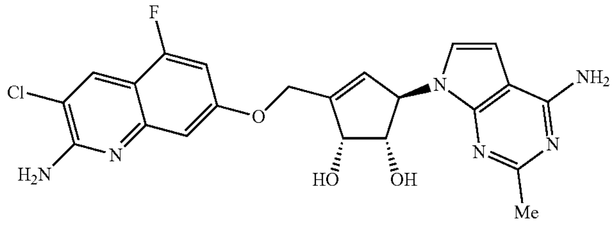 [SMILES: Cc1nc(N)c2ccn([C@@H]3C=C(COc4cc(F)c5cc(Cl)c(N)nc5c4)[C@@H](O)[C@H]3O)c2n1] (1S,2R,5R)-5-(4-Amino-2-methyl-7H-pyrrolo[2,3-d]pyrimidin-7-yl)-3-(((2-amino-3-chloro-5-fluoroquinolin-7-yl)oxy)methyl)cyclopent-3-ene-1,2-diol | tert-Butyl(7-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-2-methyl-7H-pyrrolo[2,3-d]pyrimidin-4-yl)(tert-butoxycarbonyl)carbamate | $^{1}H$ NMR (400 MHz, DMSO-$d_6$) δ 8.09 (s, 1H), 7.14 (s, 2H), 6.94 (d, J = 3.7 Hz, 3H), 6.86-6.80 (m, 2H), 6.54 (d, J = 3.6 Hz, 1H), 5.81-5.75 (m, 1H), 5.61 (d, J = 5.2 Hz, 1H), 5.17 (d, J = 6.4 Hz, 2H), 4.92-4.77 (m, 2H), 4.56 (t, J = 5.9Hz, 1H), 4.15 (q, J = 5.6 Hz, 1H), 2.38 (s, 3H).; LCMS m/z = 471.11 (M+; 50%). |
| Example-4: | tert-Butyl(1-((3aS,4R,6aR)-6-(2-(2- | $^{1}H$ NMR (400 MHz, |

TABLE 1-continued

| Structure & IUPAC name | Intermediate used | $^1$H NMR & LCMS data |
|---|---|---|
| 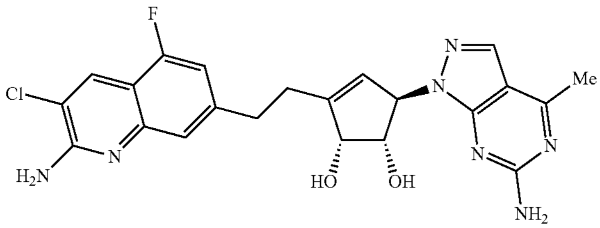 [SMILES: Cc1nc(N)nc2c1cnn2[C@@H]1C=C(CCc2cc(F)c3cc(Cl)c(N)nc3c2)[C@@H](O)[C@H]1O] (1S,2R,5R)-3-(2-(2-Amino-3-chloro-5-fluoroquinolin-7-yl)ethyl)-5-(6-amino-4-methyl-1H-pyrazolo[3,4-d]pyrimidin-1-yl)cyclopent-3-ene-1,2-diol | (bis(4-methoxybenzyl)amino)-3-chloro-5-fluoroquinolin-7-yl)ethyl)-2,2-dimethyl-3a,6a-dihydro-4H-cyclopenta[d][1,3]dioxol-4-yl)-4-methyl-1H-pyrazolo[3,4-d]pyrimidin-6-yl)(tert-butoxycarbonyl)carbamate | DMSO-d6) δ 8.16 (s, 1H), 7.99 (s, 1H), 7.21 (s, 1H), 7.05-6.90 (m, 3H), 6.74 (s, 2H), 5.51-5.41 (m, 2H), 5.00-4.85 (m, 2H), 4.45 (t, J = 5.9 Hz, 1H), 4.35-4.26 (m, 1H), 2.99-2.82 (m, 2H), 2.5-2.53 (m, 5H); LCMS m/z = 469.98 (M+; 10%). |

Example-5: (1S,2R,5R)-5-(4-Amino-2-methyl-7H-pyrrolo[2,3-d]pyrimidin-7-yl)-3-(((6-(difluoromethyl)-1,2,3,4-tetrahydroisoquinolin-8-yl)oxy)methyl)cyclopent-3-ene-1,2-diol

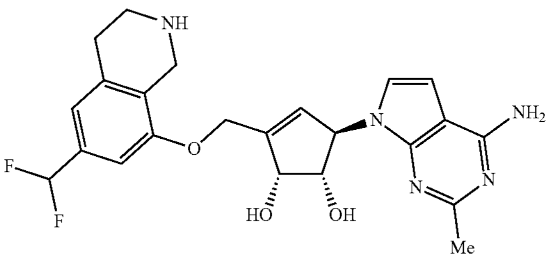 [SMILES: Cc1nc(N)c2ccn([C@@H]3C=C(COc4cc(C(F)F)cc5c4CNCC5)[C@@H](O)[C@H]3O)c2n1]

To a stirred solution of tert-butyl 8-(((3aS,4R,6aR)-4-(4-amino-2-methyl-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-3,4-dihydroisoquinoline-2(1H)-carboxylate (0.190 g, 0.318 mmol) in dioxane (3 ml) was added dioxane HCl (1.590 ml, 6.36 mmol) at 0° C. and stirred the reaction mixture at 25° C. for 3 h. Volatiles were removed in vacuo and basified with methanolic ammonia (7N). Volatiles were removed in vacuo to dryness and the crude residue was purified by reverse phase preparative HPLC (YMC Triart C18 250×50 mm, 10 m) with gradient elution of mobile phase B in mobile phase A (100% mobile phase A to 20:80 mobile phase A: mobile phase B; Mobile Phase A: Water:$CH_3CN$ (95:5, V/V)+0.1% $NH_4OH$, Mobile Phase B: $CH_3CN$:Water (90:10, V/V)+0.1% $NH_4OH$; Wavelength: 220 nm; Flow Rate: 117 ml/min; Run time: 25 min) to afford the title compound (0.021 g, 14.44%) as an off white solid. 1H NMR (400 MHz, DMSO-d6) δ 6.99 (s, 1H), 6.92 (s, 1H), 6.90 (s, 1H), 6.86 (d, J=3.6 Hz, 3H), 6.49 (d, J=3.5 Hz, 1H), 5.73 (d, J=1.9 Hz, 1H), 5.62 (d, J=4.1 Hz, 1H), 5.11 (dd, J=13.4, 6.6 Hz, 2H), 4.78 (s, 2H), 4.56 (t, J=6.0 Hz, 1H), 4.12-4.08 (m, 1H), 3.79 (s, 2H), 2.88 (t, J=5.7 Hz, 2H), 2.70-2.65 (m, 2H), 2.55 (s, 3H); LCMS m/z=458.17 (M+; 20%).

Examples in table-2 were synthesized by following an analogous reaction protocol as was used for the preparation of (1S,2R,5R)-5-(4-amino-2-methyl-7H-pyrrolo[2,3-d]pyrimidin-7-yl)-3-(((6-(difluoromethyl)-1,2,3,4-tetrahydroisoquinolin-8-yl)oxy)methyl)cyclopent-3-ene-1,2-diol using the appropriate starting materials.

| Structure & IUPAC name | Intermediate used | $^{1}$H NMR & LCMS data |
|---|---|---|
| Example-6:<br>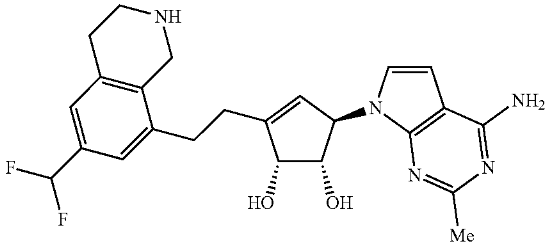 [SMILES: Cc1nc(N)c2ccn([C@@H]3C=C(CCc4cc(C(F)F)cc5c4CNCC5)[C@@H](O)[C@H]3O)c2n1]<br>(1S,2R,5R)-5-(4-Amino-2-methyl-7H-pyrrolo[2,3-d]pyrimidin-7-yl)-3-(2-(6-(difluoromethyl)-1,2,3,4-tetrahydroisoquinolin-8-yl)ethyl)cyclopent-3-ene-1,2-diol | tert-Butyl 8-(2-((3aS,4R,6aR)-4-(4-amino-2-methyl-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-3,4-dihydroisoquinoline-2(1H)-carboxylate | $^{1}$H NMR (400 MHz, DMSO-d6) δ 7.20 (s, 1H), 7.12 (s, 1H), 7.01-6.79 (m, 3H), 6.76 (d, J = 3.5 Hz, 1H), 6.46 (d, J = 3.5 Hz, 1H), 5.53 (d, J = 4.2 Hz, 1H), 5.48 (t, J = 1.7 Hz, 1H), 4.99 (d, J = 6.1 Hz, 1H), 4.95 (d, J = 6.4 Hz, 1H), 4.46 (t, J = 5.8 Hz, 1H), 3.99 (q, J = 5.5 Hz, 1H), 3.90 (s, 2H), 2.91 (t, J = 5.8 Hz, 2H), 2.83-2.71 (m, 4H), 2.44 (d, J = 9.3 Hz, 2H), 2.36 (s, 3H); LCMS m/z = 456.4 (M + 1; 20%). |

Example-7: (1S,2R,5R)-5-(4-Amino-2-methyl-7H-pyrrolo[2,3-d]pyrimidin-7-yl)-3-(2-(2-amino-3-chloro-5-fluoroquinolin-7-yl)ethyl)cyclopent-3-ene-1,2-diol

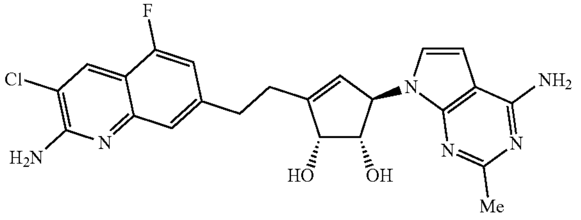 [SMILES: Cc1nc(N)c2ccn([C@@H]3C=C(CCc4cc(F)c5cc(Cl)c(N)nc5c4)[C@@H](O)[C@H]3O)c2n1]

A mixture of 7-(2-((3aS,4R,6aR)-4-(4-amino-2-methyl-7H-pyrrolo[2,3-d]pyrimidin-7-yl)-2,2-dimethyl-3a,6a-dihydro-4H-cyclopenta[d][1,3]dioxol-6-yl)ethyl)-3-chloro-5-fluoroquinolin-2-amine (0.040 g, 0.079 mmol) and TFA (0.605 ml, 7.86 mmol) was stirred at 25° C. for 1 h. Volatiles were removed in vacuo and basified with 7N methanolic ammonia. Again volatiles were removed in vacuo to dryness and the crude residue was purified by combiflash ($R_f$200, Teledyne/Isco) instrument onto a Redisep® $R_f$ column with gradient elution (0 to 7%) of methanol in dichloromethane to afford the title compound (0.033 g, 90%) as an off white solid. $^{1}$H NMR (400 MHz, DMSO-d6) δ 8.17 (s, 1H), 7.21 (s, 1H), 7.01 (dd, J=11.0, 1.4 Hz, 1H), 6.96 (s, 2H), 6.84 (s, 2H), 6.54 (d, J=3.5 Hz, 1H), 6.36 (d, J=3.5 Hz, 1H), 5.54-5.47 (m, 1H), 5.43-5.38 (m, 1H), 4.98 (d, J=6.3 Hz, 1H), 4.94 (d, J=6.6 Hz, 1H), 4.45 (t, J=6.1 Hz, 1H), 3.97-3.89 (m, 1H), 2.99-2.89 (m, 2H), 2.60-2.54 (m, 2H), 2.35 (s, 3H); LCMS m/z=469.17 (M+; 20%).

Example-8: (1S,2R,5R)-5-(2-Amino-4-methyl-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol

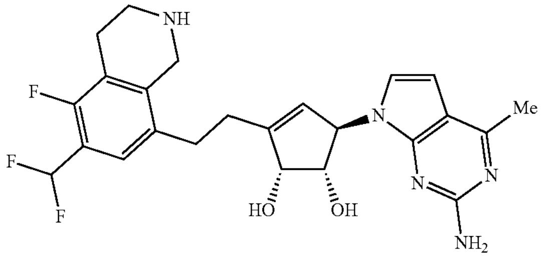 [SMILES: Cc1nc(N)nc2c1ccn2[C@@H]1C=C(CCc2cc(C(F)F)c(F)c3c2CNCC3)[C@@H](O)[C@H]1O]

A mixture of tert-butyl (tert-butoxycarbonyl)(7-((3aS,4R,6aR)-6-(2-(6-(difluoromethyl)-5-fluoro-1,2,3,4-tetrahydroisoquinolin-8-yl)ethyl)-2,2-dimethyl-3a,6a-dihydro-4H-cyclopenta[d][1,3]dioxol-4-yl)-4-methyl-7H-pyrrolo[2,3-d]pyrimidin-2-yl)carbamate (0.250 g, 0.350 mmol) and TFA (1.349 ml, 17.51 mmol) was stirred at room temperature for 15 h. Volatiles were removed in vacuo and basified with 7N methanolic ammonia. This crude residue was purified by reverse phase preparative HPLC (YMC Triart C18 250×50 mm, 10 μm) with gradient elution of mobile phase B in mobile phase A (100% mobile phase A to 20:80 mobile phase A: mobile phase B; Mobile Phase A: Water:$CH_3CN$ (95:5, V/V)+0.1% $NH_4OH$, Mobile Phase B: $CH_3CN$:Water (90:10, V/V)+0.1% $NH_4OH$; Wavelength: 220 nm; Flow Rate: 117 ml/min; Run time: 24 min) to afford the title compound (0.047 g, 28.3%) as a pale yellow solid. $^1H$ NMR (400 MHz, DMSO-d6) δ 7.33-6.99 (m, 2H), 6.72 (d, J=3.7 Hz, 1H), 6.36 (d, J=3.6 Hz, 1H), 6.08 (s, 2H), 5.50-5.42 (m, 2H), 4.95 (dd, J=15.8, 6.2 Hz, 2H), 4.47 (t, J=5.8 Hz, 1H), 3.99 (s, 3H), 3.17 (d, J=3.5 Hz, 1H), 3.05-3.00 (m, 1H), 2.87-2.63 (m, 5H), 2.56 (s, 1H), 2.41 (s, 3H). LCMS m/z=474.36 (M+; 20%).

BIOLOGICAL EXAMPLES

Biochemical Assay Protocol 1

Inhibitory effect of compounds on PRMT5 was assessed using HTRF detection technology in biochemical assay. Biotinylated H4R3 (residues 1-21) was used as a substrate. Compounds were pre-incubated with 15-25 ng PRMT5: MEP50 per well of a 384-well plate for 30 min at room temperature in the assay buffer containing 20 mM Bicine, pH 7.6, 25 mM NaCl, 2 mM DTT, 0.01% Chicken albumin and 0.01% Tween-20. Reaction was initiated by adding 1 μM of SAM and 50 nM biotinylated H4R3. Total assay volume was 15 μL. Reaction was continued for 120 min at room temperature. Then detection solution containing Streptavidin-Eu cryptate, anti-rabbit IgG-XL-665, Histone H4R3 Dimethyl Symmetric (H4R3me2s) Polyclonal Antibody, all prepared in HTRF detection buffer was added and further incubated for 30 min at room temperature. HTRF signal was recorded in PHERAStar microplate reader. Ratio of signal obtained at 665 nm and 620 nm was used to compute the percent inhibition of compound as follows % Inhibition=100−((Test Ratio−Negative control Ratio)/(Positive control Ratio−Negative control Ratio)*100) where Positive control=PRMT5+SAM+H4R3

Negative control=PRMT5+H4R3

Biochemical Assay Protocol 2

Inhibitory effect of compounds on PRMT5 was assessed using HTRF detection technology in biochemical assay. Biotinylated H4R3 (residues 1-21) was used as a substrate. Compounds were pre-incubated with 2.5 ng PRMT5: MEP50 per well of a 384-well plate for 30 min at room temperature in the assay buffer containing 20 mM Bicine, pH 7.6, 25 mM NaCl, 2 mM DTT, 0.01% Chicken albumin and 0.01% Tween-20. Reaction was initiated by adding 1 μM of SAM and 50 nM biotinylated H4R3. Total assay volume was 15 μL. Reaction was continued for 4 h at room temperature. Then detection solution containing Streptavidin-Eu cryptate, anti-rabbit IgG-XL-665, Histone H4R3 Dimethyl Symmetric (H4R3me2s) Polyclonal Antibody, all prepared in HTRF detection buffer was added and further incubated for 30 min at room temperature. HTRF signal was recorded in PHERAStar microplate reader. Ratio of signal obtained at 665 nm and 620 nm was used to compute the percent inhibition of compound as follows % Inhibition=100−((Test Ratio−Negative control Ratio)/(Positive control Ratio−Negative control Ratio)*100) where Positive control=PRMT5+SAM+H4R3

Negative control=PRMT5+H4R3

| Activity Range | Example # |
|---|---|
| $IC_{50}$ 400 pM to 750 pM | 1, 2, 3, 4, 7, 8 |
| $IC_{50}$ > 750 pM | 5, 6 |

SDMA Inhibition Assay

Protocol

Z-138 cells (ATCC, CRL-3001™) were seeded at a density of 1 million cells/well in transparent, flat bottomed tissue culture grade 48-well plates. Cells were treated with various concentration of test compounds for a period of 48 h. Cell lysate was prepared using 1×CST Lysis buffer (Cell Signaling Technology, USA) and 500 ng/well/50 μL of lysate in pH 9.6 carbonate buffer was coated on 96-well Maxisorb plate and incubated overnight at 4° C. The plate was washed twice in 1×PBS containing 0.05% Tween 20 and blocked in 1% BSA for 1 h at ambient temperature. Further, the plate was incubated first with primary antibody (anti-SDMA antibody; CST #13222s) at ambient temperature for 2 h and then with HRP-conjugated secondary antibody at ambient temperature for 1 h with 2 intermittent washing steps in between.

For luminescence based detection, HRP substrates (substrate A+ substrate B in a 1:1 proportion) were added followed by luminescence reading after 30 min in Synergy™ 2 reader (Biotek, USA).

For absorbance based detection, TMB substrate was added followed by addition of STOP solution (2N $H_2SO_4$) post colour development and absorbance (excitation 450 nm and emission 540 nm) was measured in Synergy™ 2 reader (Biotek, USA).

% inhibition of SDMA was calculated relative to the vehicle control samples containing media with 0.1% DMSO alone as per the formula below.

(Avg. of Untreated Control−Avg. of Test)×100

Avg. of Untreated control

The $IC_{50}$ values of individual compounds were calculated with Non Linear Regression Analysis using Graph Pad Prism (Graph Pad software, Inc, USA).

| Activity Range | Example # |
|---|---|
| $IC_{50}$ 100 pM to 1 nM | 1, 4, 7 |
| $IC_{50}$ 1.1 nM to 50 nM | 2, 3, 8 |

Anticancer Activity Assay

Z-138 cells were seeded at a density of 2000-3000 cells per well in culture media (IMDM+10% FBS). PANC-1 (ATCC, CRL-1469™) and MIA PaCa-2 (ATCC, CRL-1420™) cells were seeded at a density of 200-300 cells per well in culture media (DMEM+10% FBS). Cells were seeded in opaque, flat bottomed tissue culture grade 96-well plates and Z-138 cells (suspension) were seeded and treated on the same day with various concentrations of test compounds. PANC-1 and MIA PaCa-2 cells, being adherent, were kept for overnight settlement at standard cell culture conditions (37° C., 5% $CO_2$). On the following day, cells were treated with various concentrations of test compounds. Cells were treated with test compounds for a period of 96 h, 7 days and 10 days, for Z-138 cells, PANC-1 cells and MIA PaCa-2 cells, respectively. Cell viability was assessed using CellTiterGlo™ (Promega, USA) as per manufacturer's instructions. Relative Light Units (RLU) were read in Synergy™ 2 reader (Biotek, USA). The assay measures cellular ATP as an indicator of cell viability. RLU is proportional to the number of viable cells in the respective well.

% inhibition of cell viability was calculated relative to the vehicle control samples containing media with 0.1% DMSO alone as per the formula below.

$$\frac{(\text{Avg. of Untreated Control} - \text{Avg. of Test}) \times 100}{\text{Avg. of Untreated control}}$$

The $IC_{50}$ values of individual compounds were calculated with Non Linear Regression Analysis using Graph Pad Prism (Graph Pad software, Inc, USA).

| Activity Range | Example # |
|---|---|
| $IC_{50}$ 1 pM to 1 nM | 1, 2, 3, 4, 7 |
| $IC_{50}$ > 1 nM | 5, 6, 8 |

Anti-Cancer Assay (MIA PaCa-2)

| Activity Range | Example # |
|---|---|
| $IC_{50}$ 1 pM to 400 pM | 1, 7 |
| $IC_{50}$ 401 pM to 30 nM | 2, 3, 4 |

In Vivo Efficacy Experiments

Tumor xenograft for mantle cell lymphoma was established by injection of cells into the right flank of female NOD.CB17-Prkdc<scid>/J mice with an age between 7-11 weeks purchased from The Jackson Laboratory, USA. All animal study proposals were reviewed and approved by the Institutional Animal Ethics Committee (IAEC) prior to initiation of experimentation.

Z-138 Xenograft

For Z-138 xenograft mouse model, Z-138 cells (ATCC® CRL-3001™) were grown in IMDM medium supplemented with 10% FBS. Cells were incubated under standard conditions at 37° C. and 5% $CO_2$. For generating tumors, Z-138 cells in IMDM medium were mixed with Matrigel (Corning@ Matrigel® Basement Membrane Matrix) in a ratio of 1:1. $10\times10^6$ cells) in a volume of 200 μL were injected subcutaneously in each mouse to establish tumors. Mice were randomized into treatment groups of 8-10 mice, once tumors reached an average volume between 100 to 120 $mm^3$. Treatment was initiated on day of randomization and continued until end of the study. The Vehicle and test compound treatment groups were administered respective treatments orally, using gavage tubing, at an application volume of 10 mL/kg per mouse twice a day.

Mice were housed in individually ventilated cages (IVC) at room temperature of 22+3° C., humidity 50+20% and 12/12 h light/dark cycle. All the experimental activities were carried-out inside the biosafety cabinets to ensure sterility.

Tumor size was measured with Digimatic Vernier caliper (Mitutoyo, Japan) when the tumors became palpable. Tumor volume (T. V.) is calculated by using the formula:

$$\text{Tumor volume (mm3)} = (L \times W2)/2$$

Where, L: Length of tumor, W: Width of tumor in millimeter Percent tumor growth inhibition (% TGI) is calculated using the formula:

$$\%\ \text{TGI} = [1 - (Tf - Ti)/(Cf - Ci)] \times 100$$

Where, Tf and Ti, are the final and initial tumor volumes (test compound), and Cf and Ci are the final and initial mean tumor volumes (vehicle group), respectively.

Percent tumor regression is calculated as:

$$\%\ TR:(Ti - Tf)/(Ti) \times 100$$

Where, Tf and Ti, are the final and initial tumor volumes, respectively.

MIA PaCa-2 Xenograft

Tumor fragment xenograft for pancreatic cancer cell line MIA PaCa-2 was established by implantation of tumor fragments 30-45 $mm^3$ subcutaneously into the right flank of female athymic nude FOXn1<nu>/J/*Mus musculus* mice with an age between 10-11 weeks purchased from the Jackson Laboratory, USA. All animal study proposals were reviewed and approved by the Institutional Animal Ethics Committee (IAEC) prior to initiation of experimentation.

The example #1 was tested for tumor growth inhibition in subchronic MIA PaCa-2 xenograft model using assay procedure given above; the % of tumor growth inhibition at 2 mg/kg dose was found to be 57%.

The invention claimed is:

1. A compound of formula (III), its stereoisomer, or its pharmaceutically acceptable salt, (III)

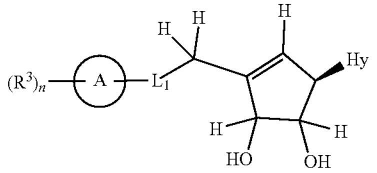

wherein the compound is (1S,2R,5R)-3-(2-(2-Amino-3-chloro-5-fluoroquinolin-7-yl)ethyl)-5-(2-amino-4-methyl-7H-pyrrolo[2,3-d]pyrimidin-7-yl)cyclopent-3-ene-1,2-diol.

2. A pharmaceutical composition comprising the compound of claim 1, its stereoisomer, or its pharmaceutically acceptable salt, and a pharmaceutically acceptable carrier.

3. A method for treating a disease, disorder, syndrome or condition associated with PRMT5 enzyme, comprising administering to a subject in need thereof an effective amount of the compound as claimed in claim 1.

4. A method as claimed in claim 3, wherein the said disease, disorder, syndrome, or condition associated with PRMT5 enzyme is glioblastoma multiforme, prostate cancer, pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

5. A method as claimed in claim 3, wherein the said disease, disorder, syndrome, or condition associated with PRMT5 enzyme is cancer.

* * * * *